United States Patent
Govindan et al.

(10) Patent No.: US 11,284,609 B2
(45) Date of Patent: Mar. 29, 2022

(54) COMPOSITIONS AND METHODS FOR CHARACTERIZING A MICROBIOME

(71) Applicant: MarvelBiome, Inc., Woburn, MA (US)

(72) Inventors: Jothi Amaranath Govindan, Malden, MA (US); Elamparithi Jayamani, Malden, MA (US); Priti H. Chatter, Concord, MA (US); Mukesh Chatter, Concord, MA (US)

(73) Assignee: MarvelBiome, Inc., Woburn, MA (US)

(*) Notice: Subject to any disclaimer, the term of this patent is extended or adjusted under 35 U.S.C. 154(b) by 0 days.

(21) Appl. No.: 17/019,183

(22) Filed: Sep. 11, 2020

(65) Prior Publication Data

US 2021/0076649 A1 Mar. 18, 2021

Related U.S. Application Data

(60) Provisional application No. 62/988,132, filed on Mar. 11, 2020, provisional application No. 62/899,718, filed on Sep. 12, 2019.

(51) Int. Cl.
*A01K 67/033* (2006.01)
*A61K 35/62* (2006.01)
*C12N 5/07* (2010.01)

(52) U.S. Cl.
CPC .......... *A01K 67/0336* (2013.01); *A61K 35/62* (2013.01); *C12N 5/0601* (2013.01); *A01K 2217/056* (2013.01); *A01K 2267/0312* (2013.01)

(58) Field of Classification Search
None
See application file for complete search history.

(56) References Cited

U.S. PATENT DOCUMENTS

| | | | |
|---|---|---|---|
| 2003/0149995 A1 | 8/2003 | Zwaal et al. | |
| 2004/0250299 A1* | 12/2004 | Verwaerde | C12Q 1/34 800/3 |
| 2005/0160482 A1 | 7/2005 | Blakely et al. | |
| 2008/0254475 A1* | 10/2008 | Hoener | C07K 14/43545 435/6.16 |
| 2014/0255351 A1* | 9/2014 | Berstad | A61P 1/12 424/93.3 |
| 2014/0331341 A1* | 11/2014 | Pak | A01K 67/0336 800/12 |

FOREIGN PATENT DOCUMENTS

WO WO-2021/051020 A3 4/2021

OTHER PUBLICATIONS

Chen et al. Nature Scientific Reports 6:34477, pp. 1-10 (Year: 2016).*
Zhang et al. PlosOne 4, e6348, pp. 1-9 (Year: 2009).*
Shen et al. The Journal of Biological Chemistry 280, pp. 20580-20588 (Year: 2005).*
Agosta, F. et al., Apolipoprotein E epsilon4 is associated with disease-specific effects on brain atrophy in Alzheimer's disease and frontotemporal dementia, Proc Natl Acad Sci USA, 106(6):2018-22 (2009).
Alonso, A. et al., Promotion of hyperphosphorylation by frontotemporal dementia tau mutations, J Biol Chem, 279(33):34873-81 (2004).
Bonet-Costa, V. et al., The Proteasome and Oxidative Stress in Alzheimer's Disease, Antioxid Redox Signal, 25(16):886-901 (2016).
Brandt, R. et al., A *Caenorhabditis elegans* model of tau hyperphosphorylation: induction of developmental defects by transgenic overexpression of Alzheimer's disease-like modified tau, Neurobiol Aging, 30(1):22-33 (2009).
Bugiani, O. et al., Frontotemporal dementia and corticobasal degeneration in a family with a P301S mutation in tau, J Neuropathol Exp Neurol., 58(6):667-77 (1999).
Di Battista, A. et al., Alzheimer's Disease Genetic Risk Factor APOE-∊4 Also Affects Normal Brain Function, Curr Alzheimer Res., 13(11):1200-1207 (2016).
Dominy, S. et al., *Porphyromonas gingivalis* in Alzheimer's disease brains: Evidence for disease causation and treatment with small-molecule inhibitors, Sci Adv., 5(1):eaau3333 (2019).
Dorey, E., Apolipoprotein E, amyloid-beta, and neuroinflammation in Alzheimer's disease, Neurosci Bull., 30(2):317-30 (2014).
Engelborghs, S. et al., Dose dependent effect of APOE epsilon4 on behavioral symptoms in frontal lobe dementia, Neurobiol Aging, 27(2):285-92 (2006).
Farlow, M. et al., Treatment outcome of tacrine therapy depends on apolipoprotein genotype and gender of the subjects with Alzheimer's disease, Neurology, 50(3):669-77 (1998).
Fijan, Sabina, Microorganisms with claimed probiotic properties: an overview of recent literature, Int J Environ Res Public Health, 11(5):4745-67 (2014).
Gonnet, G. et al., Exhaustive matching of the entire protein sequence database, Science, 256(5062):1443-5 (1992).
Grundke-Iqbal, I. et al., Abnormal phosphorylation of the microtubule-associated protein tau (tau) in Alzheimer cytoskeletal pathology, Proc Natl Acad Sci USA, 83(13):4913-7 (1986).
Holtzman, D. et al., Apolipoprotein E and apolipoprotein E receptors: normal biology and roles in Alzheimer disease, Cold Spring Harb Perspect Med., 2(3):a006312 (2012).
Hutkins, R. et al., Prebiotics: why definitions matter, Curr Opin Biotechnol., 37:1-7 (2016).
Iqbal, K. et al., Tau in Alzheimer disease and related tauopathies, Curr Alzheimer Res., 7(8):656-64 (2010).

(Continued)

*Primary Examiner* — Brian Whiteman
(74) *Attorney, Agent, or Firm* — Choate, Hall & Stewart LLP; Stephanie L. Schonewald; Sowmya Subramanian

(57) ABSTRACT

A system is provided comprising a plurality of *C. elegans* cultures, where each culture comprises a transgenic *C. elegans* strain that models a mammalian disease or condition. Methods of using a system, e.g., for characterizing microbial strains of a mammalian microbiome and determining whether such microbial strains affect a mammalian disease or disorder.

20 Claims, 7 Drawing Sheets

Specification includes a Sequence Listing.

(56) References Cited

OTHER PUBLICATIONS

Johnson, Gail V.W., Tau phosphorylation and proteolysis: insights and perspectives, J Alzheimers Dis., 9(3 Suppl):243-50 (2006).
Kanekiyo, T. et al., ApoE and Aβ in Alzheimer's disease: accidental encounters or partners?, Neuron, 81(4):740-54 (2014).
Kim, J. et al., The role of apolipoprotein E in Alzheimer's disease, Neuron, 63(3):287-303 (2009).
Lambert, J. et al., Genome-wide association study identifies variants at CLU and CR1 associated with Alzheimer's disease, Nat Genet., 41(10):1094-9 (2009).
Link, C. et al., The beta amyloid peptide can act as a modular aggregation domain, Neurobiol Dis., 32(3):420-5 (2008).
Link, Christopher D., Expression of human beta-amyloid peptide in transgenic *Caenorhabditis elegans*, Proc Natl Acad Sci USA, 92(20):9368-72 (1995).
Mahley, Robert W., Apolipoprotein E: from cardiovascular disease to neurodegenerative disorders, J Mol Med (Berl), 94(7):739-46 (2016).
Michaelson, Daniel M., APOE ϵ4: the most prevalent yet understudied risk factor for Alzheimer's disease, Alzheimers Dement., 10(6):861-8 (2014).
Mucke, L. and Selkoe, D., Neurotoxicity of amyloid β-protein: synaptic and network dysfunction, Cold Spring Harb Perspect Med., 2(7):a006338 (2012).
Oddo, Salvatore, The ubiquitin-proteasome system in Alzheimer's disease, J Cell Mol Med., 12(2):363-73 (2008).
Poppek, D. et al., Phosphorylation inhibits turnover of the tau protein by the proteasome: influence of RCAN1 and oxidative stress, Biochem J., 400(3):511-20 (2006).
Qiu, W. et al., Angiotensin converting enzyme inhibitors and the reduced risk of Alzheimer's disease in the absence of apolipoprotein E4 allele, J Alzheimers Dis., 37(2):421-8 (2013).
Ren, Q. et al., Effects of tau phosphorylation on proteasome activity, FEBS Lett., 581(7):1521-8 (2007).
Risner, M. et al., Efficacy of rosiglitazone in a genetically defined population with mild-to-moderate Alzheimer's disease, Pharmacogenomics J., 6(4):246-54 (2006).
Roses, Allen D., Apolipoprotein E alleles as risk factors in Alzheimer's disease, Annu Rev Med., 47:387-400 (1996).
Safieh, M. et al., ApoE4: an emerging therapeutic target for Alzheimer's disease, BMC Med., 17(1):64,17 pages (2019).
Shen, L. and Jia, J., An Overview of Genome-Wide Association Studies in Alzheimer's Disease, Neurosci Bull., 32(2):183-90 (2016).
Shi, Y. et al., ApoE4 markedly exacerbates tau-mediated neurodegeneration in a mouse model of tauopathy, Nature, 549(7673):523-527 (2017).
Sperling, R. et al., Amyloid-related imaging abnormalities in patients with Alzheimer's disease treated with bapineuzumab: a retrospective analysis, Lancet Neurol, 11(3):241-9 (2012).
Stevens, M. et al., Apolipoprotein E gene and sporadic frontal lobe dementia, Neurology, 48(6):1526-9 (1997).
Strittmatter, WJ, and Roses, AD., Apolipoprotein E and Alzheimer's disease, Annu Rev Neurosci., 19:53-77 (1996).
Upadhya, S and Hegde, A., Role of the ubiquitin proteasome system in Alzheimer's disease, BMC Biochem, 8 Suppl 1(Suppl 1):S12 (2007).
Van Dyck, Christopher H., Anti-Amyloid-β Monoclonal Antibodies for Alzheimer's Disease: Pitfalls and Promise, Biol Psychiatry, 83(4):311-319 (2018).
Verghese, P. et al., ApoE influences amyloid-β (Aβ) clearance despite minimal apoE/Aβ association in physiological conditions, Proc Natl Acad Sci USA, 110(19):E1807-16 (2013).
Yajima, R. et al., ApoE-isoform-dependent cellular uptake of amyloid-β is mediated by lipoprotein receptor LR11/SorLA, Biochem Biophys Res Commun., 456(1):482-8 (2015).
Zepa, L. et al., ApoE4-Driven Accumulation of Intraneuronal Oligomerized Aβ42 following Activation of the Amyloid Cascade In Vivo Is Mediated by a Gain of Function, Int J Alzheimers Dis., 2011(792070), 8 pages (2011).
Zhan, X. et al., Gram-negative bacterial molecules associate with Alzheimer disease pathology, Neurology, 87(22):2324-2332 (2016).
Zheng, Q. et al., Dysregulation of Ubiquitin-Proteasome System in Neurodegenerative Diseases, Front Aging Neurosci, 8:303 (2016).
Pryor, R. et al., Host-Microbe-Drug-Nutrient Screen Identifies Bacterial Effectors of Metformin Therapy, Cell, 178(6):1299-1312 (2019).
International Search Report for PCT/US20/50585 (Compositions and Methods for Characterizing a Microbiome, filed Sep. 11, 2020) received by ISA/US, 5 pages (dated Mar. 1, 2021).
Lublin, A.L. and Link, C.D., Alzheimer's Disease Drug Discovery: In Vivo Screening Using Caenorhabditis Elegans as a Model for B-Amyloid Peptide-Induced Toxicity, Drug Discovery Today: Techologies, 10(1):115-119 (2013).
Written Opinion for PCT/US20/50585 (Compositions and Methods for Characterizing a Microbiome, filed Sep. 11, 2020) received by ISA/US, 7 pages (dated Mar. 1, 2021).

\* cited by examiner

COMPOSITIONS AND METHODS FOR CHARACTERIZING A MICROBIOME

CROSS REFERENCE TO RELATED APPLICATIONS

The present application claims priority to U.S. provisional patent application No. 62/899,718, filed Sep. 12, 2019, and U.S. provisional patent application No. 62/988,132, filed Mar. 11, 2020, the entire contents of all of which are hereby incorporated by reference in their entirety.

SEQUENCE LISTING

The present specification makes reference to a Sequence Listing (submitted electronically as a .txt file named "2013404-0024_ST25.txt" on Nov. 10, 2020). The .txt file was generated on Oct. 7, 2020, and is 7,072 bytes in size. The entire contents of the Sequence Listing are herein incorporated by reference.

BACKGROUND

*Caenorhabditis elegans* is a bacteriovorus nematode that is about 1 mm in length and lives in temperate soil environments.

SUMMARY

The present disclosure provides an insight that *C. elegans* can provide and/or represent surprisingly useful systems for assessing one or more features of a microbial preparation (e.g., of a microbiome sample). Among other things, the present disclosure describes technologies that can be useful for assessing microbiome samples to identify or characterize effects and/or modulation of microbial strains of such microbiome samples on certain diseases or conditions. In some embodiments, such technologies can be useful to discern strain-level differences in a particular patient or patient population. Accordingly, the present disclosure also provides technologies that can be useful to assess the nature of the microbial strains in patient-specific samples and thus provide patient-specific information on how individual patients' microbiomes differentially affect their health conditions. For example, in some embodiments, technologies provided herein can be useful to identify diseases or conditions to which a patient might be susceptible, based on the nature of the microbial strains in patient-specific samples. In some embodiments, technologies provided herein can be useful to identify microbial strains in patients that are beneficial, e.g., to protect patients from or confer resistance to certain diseases or conditions. Thus, technologies described herein are useful as diagnostic tools for screening microbiome samples (e.g., human microbiome samples) for disease modifiers (e.g., microbial strains that affect a disease or condition).

Indeed, in certain embodiments, the use of transgenic *C. elegans* whole-animal model systems to identify or screen for microbiome strains (e.g., present in human microbiome) that can modulate or affect pathogenesis and/or development of a neurodegenerative disease or condition (e.g., Alzheimer's disease). Those skilled in the art reading the present disclosure will understand that technologies described herein are applicable for use not only relating to neurodegenerative diseases, such as Alzheimer's disease as exemplified, but also relating to various other diseases or conditions that may be associated with microbiomes, such as, but not limited to Parkinson's disease, Huntington's disease, and amyotrophic lateral sclerosis, type II diabetes, obesity, hyperglycemia, glucose intolerance, insulin resistance (i.e., hyperinsulinemia, metabolic syndrome, syndrome X), hypercholesterolemia, hypertension, hyperlipoproteinemia, hyperlipidemia (e.g., dyslipidemia), hypertriglyceridemia, cardiovascular disease, atherosclerosis, peripheral vascular disease, kidney disease, ketoacidosis, thrombotic disorders, nephropathy, diabetic neuropathy, diabetic retinopathy, retinopathy of prematurity, age-related macular degeneration, glaucoma, sexual dysfunction, dermatopathy, dyspepsia, hypoglycemia, metabolic syndrome, cancer or edema.

In some aspects, provided herein are systems comprising a plurality of *C. elegans* cultures, wherein each culture comprises a transgenic *C. elegans* strain that models a disease or condition (e.g., a mammalian disease or condition). In some embodiments, such a plurality of *C. elegans* cultures may comprise at least 5 or more (including, e.g., at least 6, at least 7, at least 8, at least 9, at least 10, at least 15, at least 20, at least 25, at least 30, at least 40, at least 50 or more) *C. elegans* cultures.

In some embodiments, one or more of *C. elegans* cultures in a provided system includes a transgenic *C. elegans* strain that models a disease or condition present in a target subject. In some embodiments, one or more of *C. elegans* cultures in a provided system may include a transgenic *C. elegans* strain that models a mammalian disease or condition (e.g., a human disease or condition). An exemplary human disease or condition to be modeled by *C. elegans* strains may include a neurodegenerative disease or disorder (e.g., Alzheimer's disease). In some embodiments, a disease or condition (e.g. human disease or condition) to be modeled by *C. elegans* strains may include a disease or condition associated with an altered or defective HIF-1 pathway (e.g. may comprise a cellular stress response). In some embodiments, for example, the disease or condition to be modeled by *C. elegans* may be an ocular neovascular disease or disorder (e.g., diabetic retinopathy, retinopathy of prematurity, age-related macular degeneration, or glaucoma). In some embodiments, one or more of *C. elegans* cultures in a provided system may include a transgenic *C. elegans* that models a non-human mammalian disease or conditions, e.g., a canine, a feline, an equine, a bovine, an ovine, a caprine, or a porcine disease or condition.

In some embodiments, transgenic *C. elegans* strains provided in a system described herein may comprise a transgene comprising a characteristic sequence element associated with a target disease or condition (e.g., a mammalian disease or condition). Such a characteristic sequence element that is associated with a disease or condition (e.g., a mammalian disease or condition) may be or comprise a foreign gene (e.g., a mammalian gene), a DNA regulatory element (e.g., a mammalian DNA regulatory element), and/or a mammalian RNA regulatory element. Various DNA and RNA regulatory elements are known in the art; one skilled in the art will thus understand that in some embodiments, DNA regulatory elements that are associated with a disease or condition (e.g., a mammalian disease or condition) may be or comprise enhancers, promoters, silencers, insulators, locus control regions, and combination thereof. In some embodiments, RNA regulatory elements such as, e.g., untranslated regions, introns, splice sites, and combinations thereof, which are associated with a disease or condition (e.g., a mammalian disease or condition), may be used in accordance with the present disclosure.

Additionally, or alternatively, transgenic *C. elegans* strains in a provided system may comprise a transgene comprising a reporter gene. Non-limiting examples of such a reporter gene may include, but are not limited to, fluorescent, phosphorescent, and/or bioluminescent proteins.

In some embodiments involving *C. elegans* cultures, at least two or more of such cultures may each comprise a transgenic *C. elegans* strain that models the same disease or condition (e.g., a mammalian disease or condition). In some such embodiments, at least two or more of such cultures may each comprise a transgenic *C. elegans* strain that models a different biochemical or molecular pathway associated with the same disease or condition (e.g., a mammalian disease or condition). In some embodiments involving *C. elegans* cultures, all of such cultures may each comprise the same transgenic *C. elegans* strains that model the same disease or condition (e.g., a mammalian disease or condition).

In some embodiments involving *C. elegans* cultures, at least two or more of such cultures may each comprise a transgenic *C. elegans* strain that models a different disease or condition (e.g., a mammalian disease or condition).

Systems described herein can be used to characterize relationships and/or effects of microbial preparations (e.g., of a microbiome sample) with certain diseases or conditions in target subjects. Accordingly, in some embodiments, one or more *C. elegans* cultures in such a system comprise microbes of a mammalian microbiome (e.g., a human microbiome). In some embodiments, each of such *C. elegans* cultures may include microbes of a mammalian microbiome (e.g., a human microbiome). In some embodiments, one or more *C. elegans* cultures in such a system can comprise microbes of a canine, a feline, an equine, a bovine, an ovine, a caprine, or a porcine microbiome. Microbiomes used in accordance with the present disclosure may be obtained or derived from target anatomical locations of mammalian subjects. Examples of such microbiomes may include, but are not limited to cutaneous microbiomes, oral microbiomes, nasal microbiomes, gastrointestinal microbiomes, brain microbiomes, pulmonary microbiomes, and/or urogenital microbiomes.

In some embodiments, microbes in each *C. elegans* culture can comprise one or more microbial strains. In some embodiments, microbes in each culture can comprise a single microbial strain.

In some embodiments, one or more of *C. elegans* cultures can comprise a therapeutic or nutraceutical agent.

Methods for using a plurality of *C. elegans* cultures to characterize a microbiome are also provided herein. In some embodiments, a method is for screening a microbiome of an individual (e.g., a mammal, e.g., a human) to determine if a microbial strain or a combination of microbial strains affects a mammalian disease or disorder. In some embodiments, a method is for diagnosing an individual (e.g., a mammal, e.g., a human) based on one or more microbial strains in a microbiome of the individual. In some embodiments, a method is for monitoring a disease or condition progression in an individual (e.g., a mammal, e.g., a human) based on one or more microbial strains in a microbiome of the individual.

In some embodiments described herein, a is provided method comprising adding microbes obtained from a mammalian microbiome to each of *C. elegans* cultures of a system described herein. In some embodiments, microbes in each *C. elegans* culture can comprise one or more microbial strains. In some embodiments, microbes in each such culture can comprise a single microbial strain. Microbiomes used in methods described herein may be obtained or derived from target anatomical locations of mammalian subjects. Examples of such microbiomes may include, but are not limited to cutaneous microbiomes, oral microbiomes, nasal microbiomes, gastrointestinal microbiomes, brain microbiomes, pulmonary microbiomes, and/or urogenital microbiomes.

In some embodiments, a method may comprise adding a plurality of microbial strains of a mammalian microbiome to a plurality of *C. elegans* cultures, wherein a different microbial strain is added to each *C. elegans* culture, and wherein each culture comprises the same transgenic *C. elegans* strain, and the transgenic *C. elegans* strain models a mammalian disease or condition.

In some embodiments, one or more of *C. elegans* cultures can comprise a therapeutic or nutraceutical agent. Thus, in some embodiments, a method described can further comprise adding a therapeutic or nutraceutical agent to one or more of *C. elegans* cultures.

In some embodiments, a method described herein can further comprise determining one or more parameter values of a transgenic *C. elegans* strain in each of *C. elegans* cultures. In some embodiments, such parameter(s) of a transgenic *C. elegans* is/are associated with a mammalian disease or condition that such a transgenic *C. elegans* strain models. Exemplary such parameters of transgenic *C. elegans* may include biological functions or phenotypes and/or levels and/or activity of molecules (e.g., small molecules, proteins, polypeptide, or transcripts) that are associated with a mammalian disease or condition.

In some embodiments, a method may further comprise: (a) determining, before adding a microbial strain to a *C. elegans* culture, one or more parameter values of the transgenic *C. elegans* strain in such a culture, (b) determining, after adding the microbial strain to the *C. elegans* culture, the same one or more parameter values of the transgenic *C. elegans* strain in such a culture, and (c) comparing the one or more parameter values determined before adding the microbial strain with the one or more parameter values determined after adding the microbial strain.

Technologies described herein, in some embodiments, can be used to characterize microbial strain of a human biome associated with a human disease or condition. Thus, in some such embodiments, a transgenic *C. elegans* strain involved in systems and methods described herein models a human disease or condition. An exemplary human disease or condition that a transgenic *C. elegans* strain model is Alzheimer's disease. In some embodiments, a disease or condition (e.g. human disease or condition) that a transgenic *C. elegans* strain models may include a disease or condition associated with an altered or defective HIF-1 pathway (e.g. may comprise a cellular stress response). In some embodiments, for example, a disease or condition that a transgenic *C. elegans* strain models may be an ocular neovascular disease or disorder (e.g., diabetic retinopathy, retinopathy of prematurity, age-related macular degeneration, or glaucoma). In some embodiments, a disease or condition that a transgenic *C. elegans* strain models is diabetic retinopathy, retinopathy of prematurity, age-related macular degeneration, or glaucoma.

Accordingly, certain aspects described herein relate to technologies for characterizing a microbial strain of a human biome. For example, one aspect provides a method, which comprises (a) adding a microbial strain to a *C. elegans* culture comprising a transgenic *C. elegans* strain that models Alzheimer's disease, and (b) determining whether the microbial strain affects one or more parameters of the transgenic *C. elegans* strain, wherein such one or more parameters are associated with Alzheimer's disease. In some embodiments, such a transgenic *C. elegans* strain may comprise a transgene encoding a human ssApoE4 protein, a human Aβ1-42 polypeptide, or a human pseudophosphorylated tau protein.

In some embodiments, such a method further comprises: (a) determining, before adding a microbial strain to a *C. elegans* culture, one or more parameter values of the transgenic *C. elegans* strain in such a culture, (b) determining, after adding the microbial strain to the *C. elegans* culture, the same one or more parameter values of the transgenic *C. elegans* strain in such a culture, and (c) comparing the one or more parameter values determined before adding the microbial strain with the one or more parameter values determined after adding the microbial strain. Exemplary such one or more parameters include, but are not limited to, (i) a level of *C. elegans* paralysis; (ii) a level of amyloid plaques; (iii) a level of tau filaments; (iv) a level of neuroinflammation; (v) a level of proteasomal function; and/or (vi) a combination thereof.

In another aspect, the present disclosure provides a method of characterizing a microbial strain of a human biome, comprising: (a) adding the microbial strain to a *C. elegans* culture comprising a transgenic *C. elegans* strain that models a disease or condition associated with an altered or defective HIF-1 pathway, and (b) determining whether the microbial strain affects one or more parameters of the transgenic *C. elegans* strain, wherein the one or more parameters are associated with an altered or defective HIF-1 pathway. In some embodiments, such a transgenic *C. elegans* strain may comprise a transgene encoding a human prolyl hydroxylase EGLN, a human HIF transcription factor, or a human HIFα protein.

In some embodiments, such a method further comprises: (a) determining, before adding the microbial strain to a *C. elegans* culture, one or more parameter values of the transgenic *C. elegans* strain in the culture, (b) determining, after adding the microbial strain to the *C. elegans* culture, the same one or more parameter values of the transgenic *C. elegans* strain in the culture, and (c) comparing the one or more parameter values determined before adding the microbial strain with the one or more parameter values determined after adding the microbial strain.

Exemplary such one or more parameters include, but are not limited to, (i) a level of neuroinflammation; (ii) a level of proteasomal function; (iii) a level of *C. elegans* egg-laying rate; and/or (iv) a combination thereof.

A transgenic *C. elegans* strain that expresses two or more of (i) a human ssApoE4, (ii) a human Aβ1-42, (iii) a human pseudophosphorylated tau, and (iv) a UbV-GFP proteasomal marker is also within the scope of the present disclosure.

The present disclosure, among other things, also describes uses of provided transgenic *C. elegans* strains, systems, and/or methods to screen a mammalian microbiome for microbial strains that affect a mammalian disease or condition. Also, within the scope of the present disclosure includes uses of provided *C. elegans*, systems, and/or methods to characterize the effect a microbial strain of a mammalian microbiome has on a mammalian disease or condition. For example, a human microbiome can be screened/characterized using technologies provided herein in accordance with the present disclosure.

The present disclosure describes, among other things, compositions comprising one or more microbial strains. In some embodiments, a composition provided herein comprises one or more microbial strains from a mammalian microbiome, extracts thereof, and/or components thereof, which have been assessed, identified, characterized or assayed using transgenic *C. elegans* or methods as described herein. In some embodiments, a composition provided herein comprises two or more, three or more, four or more, five or more, six or more, seven or more, eight or more, nine or more, or ten or more microbial strains from a mammalian microbiome, extracts thereof, and/or components thereof, which have been assessed, identified, characterized or assayed using transgenic *C. elegans* or methods as described herein.

In some embodiments, a composition provided herein comprises two or more, three or more, four or more, five or more, six or more, seven or more, eight or more, nine or more, or ten or more microbial strains listed in TABLE 8 below.

In some embodiments, a composition provided herein comprises *Gluconacetobacter hansenii, Terrisporobacter glycolicus, Coprococcus* sp., *L. plantarum, Clostridium butyricum, Paenibacillus* sp., *Veillonella* sp., *Bifidobacterium, Bacillus subtilis, Acidaminococcus* sp., or a combination thereof. In some embodiments, a combination comprises at least two of, at least three of, at least four of, at least five of, at least six of, at least seven of, at least eight of, at least nine of, or all of *Gluconacetobacter hansenii, Terrisporobacter glycolicus, Coprococcus* sp., *L. plantarum, Clostridium butyricum, Paenibacillus* sp., *Veillonella* sp., *Bifidobacterium, Bacillus subtilis*, and *Acidaminococcus* sp.

In some embodiments, a composition is a pharmaceutical composition. In some embodiments, a composition is an ingestible item.

The present disclosure describes, among other things, methods comprising administering a composition described herein.

In some embodiments, a method of treating a disease or condition in a subject, comprising administering to a subject in need a composition as described herein. In some embodiments, a disease or condition is a neurodegenerative disease or disorder. In some embodiments, a disease or condition is Alzheimer's disease. In some embodiments, a disease or condition may be associated with an altered or defective HIF-1 pathway. In some embodiments, a disease or condition may be an ocular neovascular disease or disorder. In some embodiments, a disease or condition is diabetic retinopathy, retinopathy of prematurity, age-related macular degeneration, or glaucoma. The present disclosure describes, among other things, uses of compositions described herein. In some embodiments, a use of a composition as described herein is in the treatment of a disease or condition in a subject. In some embodiments, a disease or condition is a neurodegenerative disease or disorder. In some embodiments, a disease or condition is Alzheimer's disease. In some embodiments, a disease or condition may be associated with an altered or defective HIF-1 pathway. In some embodiments, a disease or condition may be an ocular neovascular disease or disorder. In some embodiments, a disease or condition is diabetic retinopathy, retinopathy of prematurity, age-related macular degeneration, or glaucoma.

These, and other aspects encompassed by the present disclosure, are described in more detail below and in the claims.

Definitions

The scope of the present invention is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an," as used herein, should be understood to include the plural referents unless clearly indicated to the contrary. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Administration: As used herein, the term "administration" typically refers to the administration of a composition to a subject or system to achieve delivery of an agent to the subject or system. In some embodiments, the agent is, or is included in, the composition; in some embodiments, the agent is generated through metabolism of the composition or one or more components thereof. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In many embodiments provided by the present disclosure, administration is oral administration. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. Administration of cells can be by any appropriate route that results in delivery to a desired location in a subject where at least a portion of the delivered cells or components of the cells remain viable. A period of viability of cells after administration to a subject can be as short as a few hours, e.g., twenty-four hours, to a few days, to as long as several years, i.e., long-term engraftment. In some embodiments, administration comprises delivery of a bacterial extract or preparation comprising one or more bacterial metabolites and/or byproducts but lacking fully viable bacterial cells.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Approximately: As applied to one or more values of interest, includes to a value that is similar to a stated reference value. In certain embodiments, the term "approximately" or "about" refers to a range of values that fall within ±10% (greater than or less than) of the stated reference value unless otherwise stated or otherwise evident from the context (except where such number would exceed 100% of a possible value).

Comparable: As used herein, the term "comparable" refers to two or more agents, entities, situations, sets of conditions, subjects, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Conservative: As used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein by reference in its entirety. In some embodiments, a substitution is a moderately conservative substitution wherein the substitution has a nonnegative value in the PAM250 log-likelihood matrix.

| CONSERVATIVE AMINO ACID SUBSTITUTIONS | | |
| --- | --- | --- |
| For Amino Acid | Code | Replace With |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Determining, measuring, evaluating, assessing, assaying and analyzing: Determining, measuring, evaluating, assessing, assaying and analyzing are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Dosage form: Those skilled in the art will appreciate that the term "dosage form" may be used to refer to a physically discrete unit of an agent (e.g., a therapeutic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population.

Engineered: In general, the term "engineered" refers to the aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity, we note that, as used in the present disclosure, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Improve, increase, enhance, inhibit or reduce: As used herein, the terms "improve," "increase," "enhance," "inhibit," "reduce," or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. In some embodiments, an isolated substance or entity may be enriched; in some embodiments, an isolated substance or entity may be pure. In some embodiments, isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "enriched", "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. Those skilled in the art are aware of a variety of technologies for isolating (e.g., enriching or purifying) substances or agents (e.g., using one or more of fractionation, extraction, precipitation, or other separation).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue, capsules, powders, etc. In some embodiments, an active agent may be or comprise a cell or population of cells (e.g., a culture, for example of an EES microbe); in some embodiments, an active agent may be or comprise an extract or component of a cell or population (e.g., culture) of cells. In some embodiments, an active agent may be or comprise an isolated, purified, or pure compound. In some embodiments, an active agent may have been synthesized in vitro (e.g., via chemical and/or enzymatic synthesis). In some embodiments, an active agent may be or comprise a natural product (whether isolated from its natural source or synthesized in vitro).

Pharmaceutically acceptable: As used herein, the term "pharmaceutically acceptable" which, for example, may be used in reference to a carrier, diluent, or excipient used to formulate a pharmaceutical composition as disclosed herein, means that the carrier, diluent, or excipient is compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be is "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete, for example, when onset of a disease, disorder or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Risk: As will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90, or up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Small molecule: As used herein, the term "small molecule" refers to small organic or inorganic molecules of molecular weight below about 3,000 Daltons. In general, small molecules may have a molecular weight of less than 3,000 Daltons (Da). Small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Subject: As used herein, the term "subject" refers to an individual to which a provided treatment is administered. In some embodiments, a subject is animal. In some embodiments, a subject is a mammal, e.g., a mammal that experiences or is susceptible to a disease, disorder, or condition as described herein. In some embodiments, an animal is a vertebrate, e.g., a mammal, such as a non-human primate, (particularly a higher primate), a sheep, a dog, a rodent (e.g. a mouse or rat), a guinea pig, a goat, a pig, a cat, a rabbit, or a cow. In some embodiments, an animal is a non-mammal animal, such as a chicken, an amphibian, a reptile, or an invertebrate model C. elegans. In some embodiments, a subject is a human. In some embodiments, a patient is suffering from or susceptible to one or more diseases, disorders or conditions as described herein. In some embodiments, a patient displays one or more symptoms of a one or more diseases, disorders or conditions as described herein. In some embodiments, a patient has been diagnosed with one or more diseases, disorders or conditions as described herein. In some embodiments, the subject is receiving or has received certain therapy to diagnose and/or to treat a disease, disorder, or condition. In another embodiment, the subject is an experimental animal or animal substitute as a disease model.

Substantially: As used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more of established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION OF CERTAIN EMBODIMENTS

Figure 1:
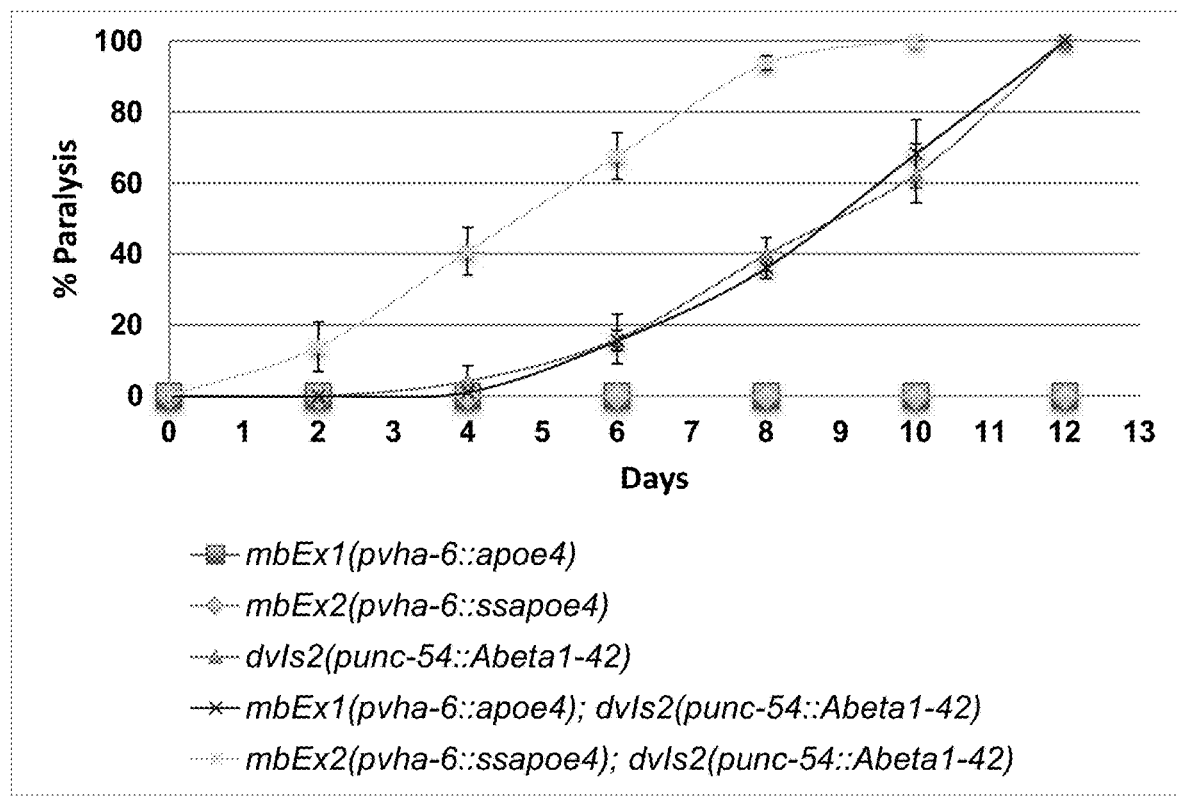
FIG. 1 shows data evidencing that APOE4 protein enhances the Aβ-induced paralysis phenotype in C. elegans. C. elegans animals having the indicated genotypes were administered an E. coli OP50 standard laboratory strain. Animals were monitored from day 1 adulthood every alternative day until all were paralyzed. For each assay, at least 20 animals were recorded. Data from three independent trials are presented in a plot. For each data point, mean±s.d is presented in the graph.

Provided herein are transgenic C. elegans disease models and methods of using C. elegans disease models to rapidly identify, assess, or characterize one or more microbial strains from a mammalian microbiome as affecting (e.g., enhancing or minimizing) a phenotype associated with a mammalian disease or condition. In some embodiments, identification, assessment, or characterization can occur with or without chemical entities and/or biologics (e.g., antibodies).

C. elegans is a bacteriovorus nematode that is fed on E. coli diet in the laboratory. C. elegans can provide reliable, effective, and efficient genotypic and phenotypic models for a number of mammalian diseases and conditions, including various human diseases and conditions, such as aging, diabetes, neurodegenerative disorders, metabolic diseases, and cancer. The present disclosure provides the insight that C. elegans models of mammalian diseases and conditions can be used to rapidly screen human microbiome for microbial strains that are affecting such mammalian diseases and conditions. It is improbable to conduct such studies in standard mammalian cell culture assays or animal models. For example, it would be economically unviable, time-consuming, and laborious to screen millions of microbial species and/or strains individually, or even in combinations using, e.g., mouse models of human diseases and conditions. While C. elegans may not include some of the complexities of mammalian systems, C. elegans models share features with mammalian systems, have quick response times, and are less expensive to produce and maintain than mammalian model systems. Accordingly, C. elegans models of mammalian diseases and conditions provide a powerful front line for examining the impacts microbial strains of mammalian biomes have on mammalian diseases and conditions and present a useful tool to prioritize lead microbial strains that impact specific and sensitive conserved therapeutic targets.

Provided herein are methods of using C. elegans as a tool for rapidly screening human microbiome for disease modifiers. Microbial strains of samples from a healthy patient or a patient having a disease or condition can be cultured using standard microbiological techniques. These microbial strains can be fed to a transgenic C. elegans strain carrying a mammalian (e.g., human) disease marker, a mammalian (e.g., human) disease gene mutation, or a combination thereof. Microbial strains can be fed to a transgenic C. elegans strain either individually or in combination. In some cases, an individual microbial strain or a combination of microbial strains can be fed to transgenic C. elegans strains that have a mammalian (e.g., human) disease marker, a mammalian (e.g., human) disease gene mutation, or a combination thereof in combination with chemical entities (e.g., small molecules, e.g., drugs) or biologics (e.g., monoclonal antibodies).

The present disclosure recognizes that multiple outcomes can arise from feeding an individual microbial strain or a combination of microbial strains can be fed to transgenic C. elegans strains that have a mammalian (e.g., human) disease marker, a mammalian (e.g., human) disease gene mutation, or a combination thereof in combination with chemical entities (e.g., small molecules, e.g., drugs) or biologics (e.g., monoclonal antibodies). In a first scenario, methods described here could be used to identify, define, assess, and/or detect individual microbial strains or combinations of microbial strains from a mammalian microbiome that increase the severity of a mammalian disease or condition phenotype in C. elegans. In a second scenario, methods described here could be used to identify, define, assess, and/or detect individual microbial strains or combinations of microbial strains from a mammalian microbiome that decrease the severity of a mammalian disease or condition phenotype in C. elegans. In a third scenario, methods described here could be used to identify, define, assess, and/or detect individual microbial strains or combinations of microbial strains from a mammalian microbiome that have no effect of a mammalian disease or condition phenotype in C. elegans. The present disclosure recognizes that each of these outcomes provides valuable information.

For example, individual microbial strains or combinations of microbial strains from a mammalian microbiome that increase the severity of a mammalian disease or condition phenotype in C. elegans can be potential early diagnostic biomarkers for a mammalian disease or condition. In some embodiments, such individual microbial strains or combinations of microbial strains are correlated with a high occurrence or increased severity of the disease or condition in mammals (e.g., human). If such a correlation has not been previously found, transgenic C. elegans and methods of using transgenic C. elegans described herein could be used to rapidly screen and/or assess one or more microbial strains in a mammalian microbiome using genetic screening or chemical extraction or genomic data mining methods to identify the potential "toxic" metabolites or components of microbiome involved in an increase in disease severity or incidence. These identified microbial strains and/or components of a mammalian microbiome could be also used for developing diagnostics. Also, identification and/or characterization of "toxic" microbial strains or microbiome components could be used for developing modulators or therapeutics that could target microbial strains, microbiome components or biosynthetic pathways that produce them.

In addition, the present disclosure recognizes that individual microbial strains or combinations of microbial strains from a mammalian microbiome that decrease the severity of a mammalian disease or condition phenotype in C. elegans can correlate with disease severity in human patients. In some embodiments, such individual microbial strains or combinations of microbial strains are correlated with a low occurrence or decreased severity of the disease or condition in mammals (e.g., human). If such a correlation has not been previously found, transgenic C. elegans and methods of using transgenic C. elegans described herein could be used to rapidly screen and/or assess one or more microbial strains in a mammalian microbiome using genetic screening or chemical extraction or genomic data mining methods to identify the potential "beneficial" microbial strains, microbiome components, or metabolites involved in an decrease in disease severity or incidence. These identified microbial strains and/or components of a mammalian microbiome could be also used for developing diagnostics. Also, identification and/or characterization of "beneficial" microbial strains or microbiome components could be used as modulators or therapeutics for disease.

In some case, individual microbial strains or combinations of microbial strains from a mammalian microbiome can be also fed in combination with chemical entities (e.g., small molecules, e.g., drugs) or biologics (e.g., monoclonal antibodies), or combinations thereof to a transgenic C. elegans strain to identify potential biological or signaling or cellular target genes or pathways. Biological or signaling or cellular target genes or pathways can include, but are not limited to, inflammation, insulin receptor, cell death, mitochondria, endoplasmic reticulum, proteasome, lipogenesis, and detoxification.

In some cases, individual microbial strains or combinations of microbial strains from a mammalian microbiome can be fed in combination with chemical entities (e.g., small molecules, e.g., drugs) or biologics (e.g., monoclonal antibodies), or combinations thereof to C. elegans strain to identify a set of signaling or target genes or pathways (e.g., a comprehensive set) that could modulate or optimize functions of a particular subcellular organelle relevant for a particular disease. For example, there are multiple pathways or targets that could be modulated to achieve optimal mitochondrial function, which is a relevant and important target in several neurodegenerative diseases, including Alzheimer's disease (AD). Biological targets for improving mitochondrial function include: biogenesis, bioenergetics, hormesis, and/or repair. Using transgenic C. elegans disease models and/or methods of using C. elegans disease models described herein, it is possible to identify individual or combinatorial microbiome species and/or combination with chemical entities (e.g., small molecules, e.g., drugs) or biologics (e.g., monoclonal antibodies), or combinations thereof that could modify or improve or alter either mitochondrial biogenesis, bioenergetics, hormesis or repair or combinations thereof. Thus, it is possible to identify and combine individual microbial strains or combinations of microbial strains from a mammalian microbiome and/or chemical entities (e.g., small molecules, e.g., drugs) or biologics (e.g., monoclonal antibodies), or combinations thereof that able to target multiple pathways to, e.g., achieve optimal mitochondrial function.

C. elegans

The free-living nematode C. elegans has been used extensively as a model system. C. elegans are inexpensive to cultivate, easy to physically manipulate, and has a multitude of genetic and molecular tools available for study. C. elegans are simple multicellular organisms: adults contain approximately 1,000 somatic cells yet have a variety of tissue types such as muscles, nerves, and intestinal cells. C. elegans have a short generation time, which allows for rapid experimentation. C. elegans generally progress from egg to larva to fertile adult in 3 days at room temperature. A single adult C. elegans can have between 300 and 1,000 progenies, which allows for a significant number of animals to be used and then quickly replenished in a relatively short amount of time. Due to the sexual dimorphism, C. elegans are useful for genetics. Self-fertilizing hermaphrodites can be maintained as homozygous mutations without the need for mating and males can be used for genetic crosses. C. elegans are transparent at every stage of their life cycle, which provides the ability to see inside the organism. This permits the observation of cellular events. It also permits the use of phosphorescent, luminescent, and fluorescent reporters.

Manipulation of protein expression in C. elegans can also be performed using RNA-mediated interference (RNAi), which can allow for rapid assessment of gene function. Another advantage of using C. elegans a model system is the ability to freeze and recover the animals, thereby allowing long-term storage.

C. elegans can be genetically modified using a number of techniques to generate transgenic C. elegans strains. The sexual dimorphism of C. elegans allows for genetic manipulations to be performed with relative ease and according to know procedures. For example, if a strain needs to be propagated, single hermaphrodites can be used to self-fertilize and generate a population of offspring. Even if a mutation renders an animal unable to mate, it remains possible for a hermaphrodite to produce progeny. Another aspect of C. elegans reproduction that makes C. elegans an effective genetic tool is the animal's ability to cross males with hermaphrodites. For example, mating experiments allow genetic markers such as mutations causing visible phenotypes to be placed together in a single organism along with an unknown mutation in order to facilitate mapping of that mutation. Hermaphrodites make only a limited number of sperm and can typically have approximately 300 self progeny. Mating increases the number of offspring produced by a single hermaphrodite to approximately 1,000 due to the addition of the male-produced sperm. The relatively large number of progeny coupled with the short life span of C. elegans allows for rapid and inexpensive analyses to be performed on the animals.

In addition to genetic modifications via reproduction, C. elegans can be genetically modified via injection of transgenes. Microinjection is an effective method for creating transgenic animals and for introducing various types of molecules directly to cells. For DNA transformation, one approach is to inject DNA into a distal arm of a C. elegans gonad. A distal germline of C. elegans contains a central core of cytoplasm that is shared by many germ cell nuclei. Therefore, DNA injected into a distal arm of a C. elegans gonad can be delivered to many progeny. Microinjection directly into oocyte nuclei can induce chromosomal integration of transgenes, but this technique can be more difficult to perform. C. elegans can also incorporate genetic material that is fed to them.

C. elegans are relatively simple to culture. C. elegans can be cultivated in either liquid culture or on the Nematode Growth Medium (NGM) agar plates in the presence of bacteria. It is possible to grow the animals in a chemically defined medium without the addition of bacteria, which can be useful because the components of a medium can be altered in order to study the nutrient or other chemical requirements of the animals. In some embodiments, C. elegans are grown on the agar plates. C. elegans can be grown on Nematode Growth Medium (NGM) agar plates. Bacteria can be spread on the NGM plates as a food source for the animals. For example, OP50, a leaky E. coli uracil auxotroph can be used. OP50 will grow slowly and provide nutrients for the animals without overgrowing them. Once the animals have eaten all of the food on a plate they will burrow into the agar and can be maintained on the "starved" plate for weeks at a time in a 15° C. incubator. The animals can be transferred to an agar plate with fresh bacteria by either cutting and moving a small block of agar from the starved plate with a sterile instrument such as a micropipette tip, or washing the worms off the surface of the plate with sterile water, or by picking one or more individuals onto a fresh plate, which will cause the C. elegans to reemerge. At any time, C. elegans can be cryogenically preserved. C.

*elegans* prefer to grow between 15° C. and 25° C., but the temperature can vary depending on the strain of *C. elegans* and conditions being tested. In some embodiments, a *C. elegans* culture can be cultured at a temperature of at least 5° C., at least 10° C., at least 15° C., at least 20° C., at least 25° C., at least 30° C., at least 35° C., or at least 40° C. In some embodiments, a *C. elegans* culture can be cultured at a temperature of at most 65° C., at most 60° C., at most 55° C., at most 50° C., at most 55° C., at most 40° C., at most 35° C., at most 30° C., at most 25° C., or at most 20° C. Standard protocols for *C. elegans* manipulation and culture are known, e.g., as described by Stiernagle T. Maintenance of *C. elegans*. Wormbook, ed. The *C. elegans* Research Community, WormBook. (Feb. 11, 2006), which is incorporated herein by reference.

Microbial Preparation(s) and/or Component(s)

The present disclosure provides systems and methods for assessing, characterizing, and identifying one or more microbial strains of a microbiome. Such systems and methods can be useful for assessing, characterizing, and identifying one or more microbial strains that affect the health of humans, livestock, and/or pets. In some embodiments, assessing, characterizing, and identifying one or more microbial strains from a microbiome of a snake, lizard, fish, or bird. In some embodiments, assessing, characterizing, and identifying one or more microbial strains from a mammalian microbiome. A mammalian microbiome can be a canine, a feline, an equine, a bovine, an ovine, a caprine, or a porcine microbiome. Generally, a microbiome used in a system or method described herein will correspond with the disease or condition modeled by a transgenic *C. elegans* used in the system or method. For example, if a transgenic *C. elegans* models a human disease, a human microbiome will be assessed, characterized, or identified.

A microbiome can be isolated from any system or tissue of an organism that supports microbial growth. For example, a microbiome can be a cutaneous microbiome, an oral microbiome, a nasal microbiome, a gastrointestinal microbiome, a brain microbiome, a pulmonary microbiome, or a urogenital microbiome. A list of exemplary microbial strains found in a gastrointestinal microbiome is included below in TABLE 8. A person skilled in the art would understand that a microbiome sample can be obtained by various ways known in the art. For example, a cutaneous, oral, nasal, pulmonary, or urogenital microbiome sample could be obtained using a swab or tissue scrapping. In some embodiments, a gastrointestinal microbiome could be sampled from feces. A cutaneous microbiome, an oral microbiome, a nasal microbiome, a gastrointestinal microbiome, a brain microbiome, a pulmonary microbiome, or a urogenital microbiome sample could be obtained via a biopsy.

In some embodiments, a microbiome is a microbiome of a healthy individual or an individual who does not suffer from or is not at risk of developing a particular disease or disorder. In some embodiments, a microbiome is a microbiome of an individual that suffers from or is at risk of developing a particular disease or disorder. In some embodiments, a microbiome is a microbiome of an individual who is known to suffer from a particular disease or disorder. In some embodiments, a human microbiome is a microbiome of a human with an unknown risk for one or more diseases or conditions.

In some embodiments, a microbiome is a reference microbiome. A reference microbiome can be a microbiome of a healthy individual or an individual who does not suffer from or is not at risk of developing a particular disease or disorder. In some instances, a reference microbiome may be from the same individual as a microbiome to be assessed or characterized, but was obtained at a different time. In some instances, a reference microbiome may be from the same individual as a microbiome to be assessed or characterized, but was obtained from a different system or tissue.

In some embodiments, an individual microbial strain or a combination of microbial strains may be assessed, characterized, or identified in a different relative amount than such strain or strains are found in a microbiome. For example, a single strain may be assessed, characterized, or identified using transgenic *C. elegans* or methods using transgenic *C. elegans* described herein, even though it is naturally present in a microbiome with other microbial strains. As another example, two microbial strains may be assessed, characterized, or identified together transgenic *C. elegans* or methods using transgenic *C. elegans* described herein, even though they are naturally present in a microbiome with additional microbial strains.

An extract, component, or compound of a microbial strain may also be assessed, characterized, or identified using transgenic *C. elegans* or methods using transgenic *C. elegans* described herein. In some cases, an extract, component, or compound of a microbial strain that has been determined to affect a transgenic *C. elegans* model of a disease or condition may be assessed, characterized, or identified. Assessing, characterizing or identifying an extract, component, or compound of a microbial strain that affect a transgenic *C. elegans* model of a disease or condition may provide additional information about potential biomarkers, targets, or protective agents in a microbiome.

A variety of technologies are known in the art that can be used to prepare extracts of microbial strains, and/or to isolate extracts, components, or compounds therefrom, or to process (e.g., to isolate and/or purify one or more components or compounds from). To give but a few examples, such technologies may include, for example, one or more of organic extraction, vacuum concentration, chromatography, and so on.

Assessing Biological Impact

The present disclosure provides the insight that *C. elegans* can be used to identify, characterize, or assess microbial strain(s) of a mammalian microbiome by contacting the microbial strain(s) (e.g., feeding the microbial strain(s) to, administering to) transgenic *C. elegans* that model a mammalian disease or condition. To determine whether a microbial strain or combination of microbial strains affects a transgenic *C. elegans* that model a mammalian disease or condition, parameters of the transgenic *C. elegans* can be observed, measured, or assessed in different samples that have been contacted with the microbial strain or combination of microbial strains. Various parameters of transgenic *C. elegans* can be observed, measured, or assessed to determine whether a microbial strain or combination of microbial strains affects a transgenic *C. elegans* that model a mammalian disease or condition. As just a few examples, transgenic *C. elegans* behaviors (e.g., mating, feeding, food aversion, or locomotion), genetic mutations (e.g., the presence of SNPs, deletions, additions, inversions, or repeats in DNA), transcript levels, protein levels, metabolite levels, lipid levels, carbohydrate levels, protein (e.g., enzyme) activity levels can be observed, measured, or assessed to determine whether a microbial strain or combination of microbial strains affects a transgenic *C. elegans* that model a mammalian disease or condition.

In some embodiments, methods described herein utilize a first sample and a second sample. In some embodiments, a first sample is a reference sample. In some embodiments, a reference sample can be a culture of transgenic *C. elegans* contacted with (e.g., administered or fed), e.g., OP50. In some embodiments, a reference sample can be a culture of transgenic *C. elegans* contacted with (e.g., administered or fed) a microbial strain or combination of microbial strains from a microbiome of a healthy individual. In some embodiments, a reference sample can be a culture of transgenic *C. elegans* contacted with (e.g., administered or fed) a microbial strain or combination of microbial strains from a microbiome of an individual obtained at a first time point.

In some embodiments, a second sample can be a test sample. In some embodiments, a test sample can be a culture of transgenic *C. elegans* contacted with (e.g., administered or fed) an individual microbial strain or a combination of microbial strains from a mammalian microbiome, e.g., a human microbiome. In some instances, a human microbiome is a microbiome of a human suffering from or at risk of a disease or condition. In some instances, a human microbiome is a microbiome of a human with an unknown risk for one or more diseases or conditions. In some embodiments, a test sample can be a culture of transgenic *C. elegans* contacted with (e.g., administered or fed) a microbial strain or combination of microbial strains from a microbiome of an individual obtained at a second time point.

In some embodiments, methods described herein comprise comparing one or more parameters obtained from a test sample with one or more parameters obtained from a reference sample. In some embodiments, by comparing one or more parameters obtained from a test sample with one or more parameters obtained from a reference sample, it can be determined that an individual microbial strain or a combination of microbial strains from a microbiome increase the severity or incidence of a disease or condition phenotype modeled by the cultured transgenic *C. elegans*. In some embodiments, by comparing one or more parameters obtained from a test sample with one or more parameters obtained from a reference sample, it can be determined that an individual microbial strain or a combination of microbial strains from a microbiome decrease the severity or incidence of a disease or condition phenotype modeled by the cultured transgenic *C. elegans*. In some embodiments, by comparing one or more parameters obtained from a test sample with one or more parameters obtained from a reference sample, it can be determined that an individual microbial strain or a combination of microbial strains from a microbiome have no effect on the severity or incidence of a disease or condition phenotype modeled by the cultured transgenic *C. elegans*.

Transgenic *C. elegans* and methods using transgenic *C. elegans* provided herein can be useful in assessing, characterizing, or identifying microbial strains of a microbiome that affect a mammalian disease or condition. The present disclosure also provides the recognition that transgenic *C. elegans* and methods using transgenic *C. elegans* provided herein can be used to define and/or characterize a microbial signature associated with a disease or condition. Further, the present disclosure provides the recognition that transgenic *C. elegans* and methods using transgenic *C. elegans* provided herein can be used to define and/or characterize a microbial signature associated with one or more features of a disease or condition (e.g., severity, responsiveness to therapy, etc.). For example, if multiple microbial strains are determined to be associated with an increased severity of a disease or disorder, e.g., across multiple individuals, the microbial strains, as well as their relative amounts, could be used as a signature to identify individuals who are at risk of developing an increased severity of the disease or disorder. As another example, if multiple microbial strains are determined to be associated with an increased severity of a disease or disorder, e.g., in a single individual, at certain times (e.g., after removal from a treatment), the microbial strains, as well as their relative amounts, could be used as a signature to identify when that individual is at risk of developing an increased severity of the disease or disorder.

The present disclosure also provides the recognition that transgenic *C. elegans* and methods using transgenic *C. elegans* provided herein can be used to diagnose an individual with a disease or condition. In fact, using a microbial signature associated with a disease or condition determined through the use of transgenic *C. elegans* and methods using transgenic *C. elegans* provided herein, an individual can be diagnosed early and/or identified as an individual at risk.

The present disclosure also provides the recognition that transgenic *C. elegans* and methods using transgenic *C. elegans* provided herein can be used to monitor progression of a disease or condition in an individual. For example, if microbial strains determined to increase the severity of a disease or condition decrease in relative amount within a microbiome, it may indicate that the disease or condition is being attenuated, e.g., by treatment or immune response.

The present disclosure also provides the insight that transgenic *C. elegans* and methods using transgenic *C. elegans* provided herein can be used to tailor treatments (e.g., therapies, nutraceuticals, and/or probiotics) to an individual patient. In some embodiments, transgenic *C. elegans* and methods using transgenic *C. elegans* provided herein can provide "personalized" therapy. In some cases, microbial strains within an individual can be assessed, characterized, or identified to determine if they have an effect on a disease or disorder. Based on the results, the individual can be treated with one or more microbial strains to adjust the microbial strains (and/or component or compound thereof) in their microbiome. In some instances, this will affect the disease or condition the individual is suffering from or at risk of developing. For example, if an individual is determined to have a relatively low amount of one or more microbial strains that have been determined to decrease the severity of a disease or condition, administration of the one or more microbial strains that have been determined to decrease the severity of a disease or condition to the individual (or an extract, component, or compound thereof) may attenuate the severity of the individual's disease or condition.

Pharmaceutical Compositions

Provided herein are compositions comprising individual microbial strains or combinations of microbial strains. In some embodiments, a composition comprises individual microbial strains or combinations of microbial strains from a mammalian microbiome, extracts thereof, and/or components thereof, which have been assessed, identified, characterized or assayed using transgenic *C. elegans* or methods as described herein. In some embodiments, a composition provided herein comprises two or more, three or more, four or more, five or more, six or more, seven or more, eight or more, nine or more, or ten or more microbial strains from a mammalian microbiome, extracts thereof, and/or components thereof, which have been assessed, identified, characterized or assayed using transgenic *C. elegans* or methods as described herein.

In some embodiments, a composition provided herein comprises two or more, three or more, four or more, five or more, six or more, seven or more, eight or more, nine or more, or ten or more microbial strains listed in TABLE 8 below.

In some embodiments, a composition provided herein comprises *Gluconacetobacter hansenii*, *Terrisporobacter*

*glycolicus, Coprococcus* sp., *L. plantarum, Clostridium butyricum, Paenibacillus* sp., *Veillonella* sp., *Bifidobacterium, Bacillus subtilis, Acidaminococcus* sp., or a combination thereof. In some embodiments, a combination comprises at least two of, at least three of, at least four of, at least five of, at least six of, at least seven of, at least eight of, at least nine of, or all of *Gluconacetobacter hansenii, Terrisporobacter glycolicus, Coprococcus* sp., *L. plantarum, Clostridium butyricum, Paenibacillus* sp., *Veillonella* sp., *Bifidobacterium, Bacillus subtilis*, and *Acidaminococcus* sp.

In some embodiments, an individual microbial strain or combinations of microbial strains from a mammalian microbiome that have been killed (e.g., heat killed). Alternatively, in some embodiments, an individual microbial strain or combinations of microbial strains from a mammalian microbiome may include cells that are viable or alive.

In some embodiments, one or more microbial strains comprise a viable or living individual microbial strain or combinations of microbial strains, e.g., from a mammalian microbiome.

In some embodiments, one or more microbial strains comprise a viable or living individual microbial strain or combinations of microbial strains, e.g., from a mammalian microbiome, as described herein comprises and/or is formulated through use of one or more cell cultures and/or supernatants or pellets thereof, and/or a powder formed therefrom.

In some embodiments, compositions for use in accordance with the present disclosure are pharmaceutical compositions, e.g., for administration (e.g., oral administration) to a mammal (e.g., a human). Pharmaceutical compositions typically include an active agent (e.g., individual microbial strains or combinations of microbial strains from a mammalian microbiome, extracts thereof, and/or components thereof), and a pharmaceutically acceptable carrier. Certain exemplary pharmaceutically acceptable carriers include, for instance saline, solvents, dispersion media, coatings, antibacterial and antifungal agents, isotonic and absorption delaying agents, and the like, compatible with pharmaceutical administration.

In some embodiments, a pharmaceutical composition for use in accordance with the present disclosure may include and/or may be administered in conjunction with, one or more supplementary active compounds; in certain embodiments, such supplementary active agents can include ginger, curcumin, probiotics (e.g, probiotic strains of one or more of the following genera: *Lactobacillus, Bifidobacterium, Saccharomyces, Enterococcus, Streptococcus, Pediococcus, Leuconostoc, Bacillus*, and/or *Escherichia coli* (see Fij an, Int J Environ Res Public Health. 2014 May; 11(5): 4745-4767, which is incorporated herein by reference); prebiotics (nondigestible food ingredients that help support growth of probiotic bacteria, e.g., fructans such as fructooligosaccharides (FOS) and inulins, galactans such as galactooligosaccharides (GOS), dietary fibers such as resistant starch, pectin, beta-glucans, and xylooligosaccharides (Hutkins et al., Curr Opin Biotechnol. 2016 February; 37: 1-7, which is incorporated herein by reference) and combinations thereof.

Pharmaceutical compositions are typically formulated to be compatible with its intended route of administration. Examples of routes of administration include oral administration. Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). Oral compositions generally include an inert diluent or an edible carrier. To give but a few examples, in some embodiments, an oral formulation may be or comprise a syrup, a liquid, a tablet, a troche, a gummy, a capsule, e.g., gelatin capsules, a powder, a gel, a film, etc.

In some embodiments, pharmaceutically compatible binding agents, and/or adjuvant materials can be included as part of a pharmaceutical composition. In some particular embodiments, a pharmaceutical composition can contain, e.g., any one or more of the following inactive ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In some embodiments, the compositions can be taken as-is or sprinkled onto or mixed into a food or liquid (such as water). In some embodiments, a composition that may be administered to mammals as described herein may be or comprise an ingestible item (e.g., a food or drink) that comprises (e.g., is supplemented) with an individual microbial strain or combinations of microbial strains from a mammalian microbiome, extracts thereof, and/or components thereof.

In some embodiments, a food can be or comprise one or more of bars, candies, baked goods, cereals, salty snacks, pastas, chocolates, and other solid foods, as well as liquid or semi-solid foods including yogurt, soups and stews, and beverages such as smoothies, shakes, juices, and other carbonated or non-carbonated beverages. In some embodiments, foods are prepared by a subject by mixing in individual microbial strains or combinations of microbial strains from a mammalian microbiome, extracts thereof, and/or components thereof.

Compositions can be included in a kit, container, pack, or dispenser, together with instructions for administration or for use in a method described herein.

Those skilled in the art, reading the present disclosure, will appreciate that, in some embodiments, a composition (e.g., a pharmaceutical composition) as described herein may be or comprise one or more cells, tissues, or organisms (e.g., plant or microbe cells, tissues, or organisms) that produce (e.g., have produced, and/or are producing) a relevant compound.

Those skilled in the art will appreciate that, in some embodiments, technologies for preparing compositions and/or preparations, and/or for preparing (and particularly for preparing pharmaceutical compositions) may include one or more steps of assessing or characterizing a compound, preparation, or composition, e.g., as part of quality control. In some embodiments, if an assayed material does not meet pre-determined specifications for the relevant assessment, it is discarded. In some embodiments, if such assayed material does meet the pre-determined specifications, then it continues to be processed as described herein.

In some embodiments, a pharmaceutical composition provided herein can promote the colonization of an individual microbial strain or combinations of microbial strains from a mammalian microbiome, particularly microbial strain(s) that have been identified, characterized, or assessed as decreasing the severity or incidence of a mammalian disease or condition, in a mammal suffering from or at risk of the mammalian disease or condition. In some embodiments, a pharmaceutical composition provided herein can attenuate the colonization of an individual microbial strain or combinations of microbial strains from a mammalian microbiome, particularly microbial strain(s) that have been identified, characterized, or assessed as increasing the severity or incidence of a mammalian disease or condition, in a mammal suffering from or at risk of the mammalian disease or condition. In some embodiments, a pharmaceutical composition provided herein can promote the colonization of an individual microbial strain or combinations of microbial strains from a mammalian microbiome, particularly microbial strain(s) that have been identified, characterized, or assessed as not affecting the severity or incidence of the mammalian disease or condition but have been identified, characterized, or assessed as being capable of outcompeting one or more microbial strains that have been identified, characterized, or assessed as increasing the severity or incidence of a mammalian disease or condition, in a mammal suffering from or at risk of the mammalian disease or condition.

In some embodiments, each of the one or more microbial strains in a composition comprises $10^1$ to $10^{12}$ colony forming units (CFUs). In some embodiments, each of the one or more microbial strains in a composition comprises $10^6$ to $10^{12}$ CFUs. In some embodiments, each of the one or more microbial strains in a composition comprises the same number of CFUs. In some embodiments, some of the one or more microbial strains in a composition comprises a different number of CFUs.

In some embodiments, a composition comprises a total of $10^6$ to $10^{12}$ of CFUs.

In some embodiments, a pharmaceutical composition is tailored to a specific mammal (e.g., a specific human patient) based on that mammal's (e.g., human's) microbiome. In some embodiments, a pharmaceutical composition is specific for a microbiome of an individual mammal (e.g., human). In some embodiments, a pharmaceutical composition is specific for microbiomes of a population of mammals (e.g., humans). Populations of mammals can include, but are not limited to: families, mammals in the same regional location (e.g., neighborhood, city, state, or country), mammals with the same disease or condition, mammals of a particular age or age range, mammals that consume a particular diet (e.g., food, food source, or caloric intake).

Methods of Treatment

The present disclosure recognizes that compositions described herein can be useful in the treatment of subjects. Methods provided by the present disclosure include methods for the treatment of certain diseases, disorders and conditions. In some embodiments, relevant diseases, disorders and conditions may be or include a neurodegenerative disease, disorder, or condition. In some embodiments, a neurodegenerative disease, disorder, or condition may be Alzheimer's disease. In some embodiments, relevant diseases, disorders and conditions may be or include an ocular neovascular disease, disorder, or condition. In some embodiments, a neurodegenerative disease, disorder, or condition may be diabetic retinopathy, retinopathy of prematurity, age-related macular degeneration, or glaucoma.

Generally, methods of treatment provided by the present disclosure involve administering a therapeutically effective amount of a composition as described herein alone or in combination with other compositions and/or treatments to a subject who is in need of, or who has been determined to be in need of, such treatment.

In some embodiments, methods of treatment provided herein are prophylactic or preventative, e.g., may be administered to subjects prior to display of significant symptoms and/or to exposure to a particular expected inducement that is associated with neurodegenerative diseases, disorders, or conditions. In some embodiments, methods of treatment provided herein are therapeutic, e.g., may be administered to subjects after development of significant symptoms associated with neurodegenerative diseases, disorders, or conditions.

In some embodiments, provided methods of treatment are administered to a subject that is a mammal, e.g., a mammal that experiences a disease, disorder, or condition as described herein; in some embodiments, a subject is a human or non-human veterinary subject, e.g., an ape, cat dog, monkey, or pig.

In many embodiments, treatment involves ameliorating at least one symptom of a disease, disorder, or condition associated with neurodegenerative diseases, disorders, or conditions. In some embodiments, a method of treatment can be prophylactic.

In some embodiments, the methods can include administration of a therapeutically effective amount of compositions disclosed herein before, during (e.g., concurrently with), or after administration of a treatment that is expected to be associated with neurodegenerative diseases, disorders, or conditions.

In some embodiments, subjects who receive treatment as described herein may be receiving and/or may have received other treatment (e.g., pharmacological treatment/therapy, surgical, etc), for example that may be intended to treat one or more symptoms or features of a disease disorder or condition as described herein (e.g. neurodegenerative diseases, disorders, or conditions), so that provided compositions are administered in combination with such other therapy (i.e. treatment) to treat the relevant disease, disorder, or condition.

In some embodiments, the compositions described herein can be administered in a form containing one or more pharmaceutically acceptable carriers. Suitable carriers have been described previously and vary with the desired form and mode of administration of a composition. For example, pharmaceutically acceptable carriers can include diluents or excipients such as fillers, binders, wetting agents, disintegrators, surface-active agents, glidants, and lubricants. Typically, a carrier may be a solid (including powder), liquid, or any combination thereof. Each carrier is preferably "acceptable" in the sense of being compatible with other ingredients in the composition and not injurious to a subject. A carrier can be biologically acceptable and inert (e.g., it permits the composition to maintain viability of the biological material until delivered to the appropriate site).

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

Oral compositions can include an inert diluent or an edible carrier. For purposes of oral therapeutic administration, an active compound can be incorporated with excipients and used in the form of tablets, lozenges, pastilles, troches, or capsules, e.g., gelatin capsules. Oral compositions can also be prepared by combining a composition of the present disclosure with a food. In some embodiments, microbes can be formulated in a food item. Some non-limiting examples of food items to be used with the methods and compositions described herein include: popsicles, cheeses, creams, chocolates, milk, meat, drinks, pickled vegetables, kefir, miso, sauerkraut, etc. In other embodiments, food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with microbial strain(s) to avoid killing any microbes. In one embodiment a food used for administration is chilled, for example, iced flavored water. In certain embodiments, the food item is not a potentially allergenic food item (e.g., not soy, wheat, peanut, tree nuts, dairy, eggs, shellfish or fish). Pharmaceutically compatible binding agents, and/or adjuvant materials can be included as part of the composition.

In some such embodiments, a composition described herein is administered to a subject according to a dosing regimen that achieves population of the subject's microbiome with administered cells. In some embodiments, a composition is administered to a subject in a single dose. In some embodiments, a composition is administered to a subject in a plurality of doses. In some embodiments, a dose of a composition is administered to a subject twice a day, daily, weekly, or monthly.

In some embodiments, each of the one or more microbial strains in a dose comprises $10^1$ to $10^{12}$ colony forming units (CFUs). In some embodiments, each of the one or more microbial strains in a dose comprises $10^6$ to $10^{12}$ CFUs. In some embodiments, each of the one or more microbial strains in a dose comprises the same number of CFUs. In some embodiments, some of the one or more microbial strains in a dose comprises a different number of CFUs.

In some embodiments, a dose of one or more microbial strains comprises a total of $10^6$ to $10^{12}$ CFUs. In some embodiments, a dose of one or more microbial strains comprises a total of $10^7$ to $10^{10}$ CFUs. In some embodiments, a dose of one or more microbial strains comprises 5-200 billion CFUs. In some embodiments, a dose of one or more microbial strains comprises 5-50 billion CFUs. In some embodiments, a dose of one or more microbial strains comprises 5-20 billion CFUs. In some embodiments, a dose of one or more microbial strains comprises 50-100 billion CFUs. In some embodiments, a dose of one or more microbial strains comprises 100-200 billion CFUs.

Examples

The following examples are provided so as to describe to the skilled artisan how to make and use methods and compositions described herein, and are not intended to limit the scope of the present disclosure.

Example 1: Materials and Methods

Two different constructs for a human APOE4 transgene under the control of an intestinal promoter (pvha-6::apoE4::tbb-2 UTR) were generated by gene synthesis. The constructs were cloned into the KpnI/SalI restriction enzyme site of pUC57 plasmid. Human APOE4 protein sequence was codon optimized for optimal expression in C. elegans. Three synthetic introns were included within the apoE4 sequence in both constructs to avoid gene silencing and optimum expression in C. elegans. The nucleotide sequences of the introns are included in TABLE 1 below.

In one construct, a signal sequence for secretion from C. elegans FLP-1 was included in the apoE4 sequence ("Worm 2"). In the other construct, no signal sequence was added to the apoE4 sequence ("Worm 1").

TABLE 1

| Element | Sequence |
| --- | --- |
| Intron 1 | gtaagtttaaacatatatatactaactaaccctga ttatttaaattttcag (SEQ ID NO: 1) |
| Intron 2 | gtaagtttaaacagttcggtactaactaaccatac atatttaaattttcag (SEQ ID NO: 2) |
| Intron 3 | gtaagtttaaacatgattttactaactaactaatc tgatttaaattttcag (SEQ ID NO: 3) |
| FLP-1 Signal Sequence | atgactctgctctaccaagtagggttattactcct tgtggcagctacttataaggtgtcggca (SEQ ID NO: 4) |

Extrachromosomal array strains were constructed by injecting the either Worm 1 or Worm 2 with an expression plasmid and co-injection marker (2 ng/μl for pCFJ90, pmyo-2::mCherry). Sequences used for Worm 1 and Worm 2 are included in TABLE 2 below. Coding sequences are indicated by capital letters; non-coding sequences are indicated by small letters.

TABLE 2

| WORM 1 |
| --- |
| vha-6 promoter: (SEQ ID NO: 5) actaactgacattaggtgtcacacaaaagaaatcacacactatacatcaa aatatacatcacaagtgagtcaatacaatccgggtgaagctcaagaatgg atttcgcagacttcttctgctcattggctgcttcgaaaacctgaatagtt tatattaaactagtgaaatcgaattcatacaaacctgtttcgattcacta cttttcaatcgatggtcaaacgtagaatcaaaaacacgtgtcagaaacac ttccaatcatcaaaatgatccatcaattccactcggagcaacaatttcga agcctgggaatgtgtgtggtgagcacttttggctctggtagagcatgtac ctttataggtgcgctctacgcaattcaccagctgaacaatggagtgagc ctaatgtaactaaaaatttatttgaatgctttacaaaaatattatttcag atcttcgagatcatgaaaactatcaaacagcagcgcctggagcaatcga gtcgttcccacaatattcaggtgtatatgcaatcgttttagactacattt cggtaagttgctacttcagagataaactgtaattattttttaaatttcagcg caaacgcggaggaaagtctgatcctgttaacaaatacataaatcgtttcc tcgctgatctcacggagatattgccagcatgctcaacgttgccagtgatg aatccaagcacagaactgcattaagtatactatttattactcgatactttt tgttcacataggttttttaaatcatattttatgcatcatttatcatattc aatgcatcattcatatcatagtcaataaaaaggttgatttctcatgttct ggtttcaaatgctgactttggtaaaaagaacgcgtgcctgcctattgcct atcttggcattttctcgataaattttaaaatgtaggttcgatcttatgag atttgtagtcaaaagagctcatatgtattcaggtaggtctggtagcgaga ccaacttaatagcatgacaagcattttcaatttgccctggagcgcaattg gttttttattcgaaaatcgcacatttctgtttccccataatataaaattt ccaggacgatatatattacattcttcacaaaatattgcattacagacacc gacaaagaatctccacctgatatgaaaacaatgagccaacaatgttatct gtattgccaccacccacatttcctagtcattcagtatatattgtttcaat tgaatcattgcaggtatatatcgaattgaacttgtaaggcttcatcttca tttctcaatacatcatccatcattccagagcagctccggccacacaaaaa ttggtggcggtctgatattgataatcgacttcttttgacgtgcctgacgga gcagcaaagcggagcactgataagacaatgaagaactaaaaaattgtctt |

TABLE 2-continued

```
cggttttcagtctttagttctgcagcactttattttttgtttctcctatt
tttccgcattttcctaactttctgatgtccatttcaaatgattttttgtta
taaaattgtttaatttcagggcgactaaaacctaccaaaacccataaaaa
``` human apoE4:

(SEQ ID NO: 6)
```
atgAAGGTCCTTTGGGCCGCCCTTCTTGTCACCTTCCTTGCTGGATGCCA
AGCTAAGGTTGAGCAAGCTGTTGAAACTGAGCCAGAGCCAGAGCTTCGTC
AACAAACTGAGTGGCAATCTGGACAACGTTGGGAGCTTGCTCTTGGACGT
TTCTGGGACTACCTTCGTTGGGTTCAAACCCTTTCCGAGCAAGTTCAAGA
GGAGCTTCTTTCTTCCCAAGTTACCCAAGAGCTTCGTGCTCTTATGGATG
AGACTATGAAGgtaagtttaaacatatatatactaactaaccctgattat
ttaaattttcagGAGCTTAAGGCTTACAAGTCTGAGCTTGAGGAGCAACT
TACCCCAGTTGCTGAGGAGACCCGTGCTCGTCTTTCCAAGgtaagtttaa
acagttcggtactaactaaccatacatatttaaattttcagGAGCTTCAA
GCTGCTCAAGCTCGTCTTGGAGCTGATATGGAGGATGTTCGTGGACGTCT
TGTTCAATACCGTGGAGAGGTTCAAGCTATGCTTGGACAATCTACCGAGG
AGCTTCGTGTTCGTCTTGCCTCCCACCTTCGTAAGCTTCGTAAGCGTCTT
CTTCGTGACGCTGACGACCTTCAAAAGCGTCTTGCTGTCTACCAAGCTGG
AGCTCGTGAGGGAGCTGAGCGTGGACTTTCCGCTATCCGTGAGCGTCTTG
GACCACTTGTTGAGCAAGGACGTGTTCGTGCTGCTACCGTCGGATCCCTT
GCTGGACAACCACTTCAAGAGCGCGCTCAAGCTTGGGGAGAGCGTCTTCG
TGCTCGCATGGAGGAGATGGGATCTCGCACCCGTGATCGTCTTGATGAGG
TTAAGgtaagtttaaacatgatttactaactaactaatctgatttaaat
tttcagGAGCAAGTTGCTGAGGTCCGTGCTAAGCTTGAAGAGCAAGCTCA
ACAAATCCGTCTTCAAGCTGAGGCTTTCCAAGCTCGTCTTAAGTCTTGGT
TCGAGCCACTTGTTGAGGATATGCAACGTCAATGGGCTGGACTTGTTGAG
AAGGTCCAAGCCGCTGTCGGAACCTCCGCTGCTCCAGTTCCATCCGATAA
CCACTAA
``` tbb-2 3'UTR:

(SEQ ID NO: 7)
```
atgcaagatcctttcaagcattccatatactatcactatattattttgtc
aaaaaattctacgctaatttatttgattttttaatgttattattttatgac
tttttatagtcactgaaaagtttgcatctgagtgaagtgaatgctatcaa
aatgtgattctgtagatgtactttcacaatctacttcaattccatttga
agtgattaaacccgaaaggttgagaaaaatgcgagcgctcaaatatttgt
attgtgttcgttgagtgacccaacaaaaagaggaaa
```

WORM 2 vha-6 promoter:

(SEQ ID NO: 5)
```
actaactgacattaggtgtgtcacacaaaagaaatcacacactatacatcaa
aatatacatcacaagtgagtcaataacaatccgggtgaagctcaagaatgg
atttcgcagacttatctgacattggctgatcgaaaacctgaaatgtttat
attaaactagtgaaatcgaattcatacaaacctgtttcgattcactactt
ttcaatcgatggtcaaacgtagaatcaaaaacacgtgtcagaaacacttc
caatcatcaaaatgatccatcaattccactcggagcaacaatttcgaagc
ctgggaatgtgtgtggtgagcacttttggactggtagagcatgtaccttt
ataggtgcgctctacgcaattcaccagagaacaatggagttgagcctaat
gtaactaaaaatttatttgaatgattacaaaaatattattttcagatatcg
agatcatgaaaactatcaaacagcagcgccaggagcaatcgagtcgttcc
cacaatattcaggtgtatatgtcaatcgttttagactacattctcggtaagt
tgctacttcagagataaaactgtaattatttttaaatttcagcgcaaacgcg
gaggaaagtagatcctgttaacaaatacataaatcgtttcctcgctgata
cacggagatattgccagcatgacaacgttgccagtgatgaatccaagcac
agaactgcattaagtatactatttattactcgatacttttgttcacatag
gttttttaaatcatattttatgcatcatttatcatatccaatgcatcatt
catatcatagtcaataaaaaggttgatttacatgttctggtttcaaatgc
tgactttggtaaaagaacgcgtgcctgcctattgcctatcttggcatttt
tacgataaattttaaatgtaggttcgatatatgagatttgtagtcaaaa
gagacatatgctttcaggtaggtaggtagcgagaccaacttaatagcatg
acaagcattttcaatttgccaggagcgcaattggttttttattcgaaaat
cgcacatttctgtttcccataatataaaatttccaggacgatatatatt
acattatcacaaaatattgcattacagacaccgacaaagaataccacctg
atatgaaaacaatgagccaacagtgttatctgtattgccaccacccacat
ttcctagtcattcagtatatattgtttcaattgaatcattgcaggtatat
atcgaattgaacttgtaaggatcatatcatttacaatacatcatccatca
ttccagagcagaccggccacacaaaaattggtggcggtagatattgataa
tcgacttattgacgtgcctgacggagcagcaaagcggagcactgataaga
caatgaagaactaaaaaattgtatcggttttcagtattagttctgcagca
ctttatttttgtttctcctattttccgcattttcctaactttctgatg
tccatttcaaatgattttttgttataaaattgtttaatttcagggcgacta
aaacctaccaaaacccataaaaa
``` human ssapoE4:

(SEQ ID NO: 8)
```
atgactctgctctaccaagtagggttattactccttgtggcagctactta
taaggtgtcggcaAAGGTCCTTTGGGCCGCCCTTCTTGTCACCTTCCTTG
```

TABLE 2-continued

```
CTGGATGCCAAGCTAAGGTTGAGCAAGCTGTTGAAACTGAGCCAGAGCCA
GAGCTTCGTCAACAAACTGAGTGGCAATCTGGACAACGTTGGGAGCTTGC
TCTTGGACGTTTCTGGGACTACCTTCGTTGGGTTCAAACCCTTTCCGAGC
AAGTTCAAGAGGAGCTTCTTTCTTCCCAAGTTACCCAAGAGCTTCGTGCT
CTTATGGATGAGACTATGAAGgtaagtttaaacatatatatactaactaa
ccctgattatttaaattttcagGAGCTTAAGGCTTACAAGTCTGAGCTTG
AGGAGCAACTTACCCCAGTTGCTGAGGAGACCCGTGCTCGTCTTTCCAAG
gtaagtttaaacagttcggtactaactaaccatacatatttaaattttca
gGAGCTTCAAGCTGCTCAAGCTCGTCTTGGAGCTGATATGGAGGATGTTC
GTGGACGTCTTGTTCAATACCGTGGAGAGGTTCAAGCTATGCTTGGACAA
TCTACCGAGGAGCTTCGTGTTCGTCTTGCCTCCCACCTTCGTAAGCTTCG
TAAGCGTCTTCTTCGTGACGCTGACGACCTTCAAAAGCGTCTTGCTGTCT
ACCAAGCTGGAGCTCGTGAGGGAGCTGAGCGTGGACTTTCCGCTATCCGT
GAGCGTCTTGGACCACTTGTTGAGCAAGGACGTGTTCGTGCTGCTACCGT
CGGATCCCTTGCTGGACAACCACTTCAAGAGCGCGCTCAAGCTTGGGGAG
AGCGTCTTCGTGCTCGCATGGAGGAGATGGGATCTCGCACCCGTGATCGT
CTTGATGAGGTTAAGgtaagtttaaacatgatttactaactaactaatc
tgatttaaattttcagGAGCAAGTTGCTGAGGTCCGTGCTAAGCTTGAAG
AGCAAGCTCAACAAATCCGTCTTCAAGCTGAGGCTTTCCAAGCTCGTCTT
AAGTCTTGGTTCGAGCCACTTGTTGAGGATATGCAACGTCAATGGGCTGG
ACTTGTTGAGAAGGTCCAAGCCGCTGTCGGAACCTCCGCTGCTCCAGTTC
CATCCGATAACCACTAA
``` tbb-2 3'UTR:

(SEQ ID NO: 7)
```
atgcaagatcctttcaagcattcccttcttctctatcactcttctttctt
tttgtcaaaaaattctctcgctaatttatttgcttttttaatgttattat
tttatgacttttatagtcactgaaaagtttgcatctgagtgaagtgaat
gctatcaaaatgtgattctgtctgatgtactttcacaatctctcttcaat
tccattttgaagtgcttaaacccgaaaggttgagaaaaatgcgagcgct
caaatatttgtattgtgttcgttgagtgacccaacaaaaagaggaaa
```

TABLE 3

| Strain | Genotype |
|---|---|
| PD1074 | C. elegans wild-type |
| MB1 | mbEx1(pvha-6::apoE4::tbb-2 UTR + pmyo-2:mCherry) |
| MB2 | mbEx2(pvha-6::ssapoE4::tbb-2 UTR + pmyo-2:mCherry); SS is signal sequence |
| MB3 | mbEx1(pvha-6::apoE4::tbb-2 UTR + pmyo-2:mCherry); dvIs37 [myo-3p:: GFP::Aβ(3-42) + rol-6(su1006)] |
| MB4 | mbEx2(pvha-6::ssapoE4::tbb-2 UTR + pmyo-2:mCherry); dvIs37 [myo-3p::GFP::Aβ (3-42) + rol-6(su1006)] |
| CL2331 | dvIs37 [myo-3p::GFP::Aβ (3-42) + rol-6(su1006)] |
| MB5 | mbEx1(pvha-6::apoE4::tbb-2 UTR + pmyo-2:mCherry); dvIs2 [pCL12(unc-54/human Aβ peptide 1-42 minigene) + pRF4] |
| MB6 | mbEx2(pvha-6::ssapoE4::tbb-2 UTR + pmyo-2:mCherry); dvIs2 [pCL12(unc-54/human Aβ peptide 1-42 minigene) + pRF4] |
| CL2006 | dvIs2 [pCL12 (unc-54/human Aβ peptide 1-42 minigene) + pRF4] |
| MB7 | mbEx3 [unc-119(+);sur-5::UbV-GFP] |
| MB8 | mbIs1[F25B3.3::tau352(PHP) + pha-1(+)] |
| MB9 | mbEx3 [unc-119(+);sur-5::UbV-GFP]; mbIs1[F25B3.3::tau352(PHP) + pha-1(+)] |
| MB10 | mbEx2(pvha-6::ssapoE4::tbb-2 UTR + pmyo-2:mCherry); mbIs1[F25B3.3::tau352(PHP) + pha-1(+)] |
| MB11 | mbEx2(pvha-6:: ssapoE4::tbb-2 UTR + pmyo-2:mCherry); mbEx3 [unc-119(+); sur-5::UbV-GFP] |
| MB12 | mbEx2(pvha-6::ssapoE4::tbb-2 UTR + pmyo-2:mCherry); mbEx3 [unc-119(+); sur-5::UbV-GFP]; mbIs1[F25B3.3::tau352(PHP) + pha-1(+)] |
| MB13 | mbEx2(pvha-6::ssapoE4::tbb-2 UTR + pmyo-2:mCherry); mbEx3 [unc-119(+); sur-5::UbV-GFP]; mbIs1[F25B3.3::tau352(PHP) + pha-1(+)]; dvIs2 [pCL12(unc-54/human Aβ peptide 1-42 minigene) + pRF4] |

Example 2: Exemplary System for Characterizing Microbial Strains that Affect a Parameter Associated with Alzheimer's Disease

Example 2.1: Alzheimer's Disease

Alzheimer's disease (AD) is the most common cause of dementia. AD is characterized by a progressive decline in cognitive functions, including memory, language, and cognitive skills. Senile plaques and intracellular neurofibrillary tangles are generally considered hallmark features of AD pathology. Plaques can comprise of aggregates of amyloid-β(Aβ) peptides of either 40 or 42 amino acids, which can be formed by abnormal processing of amyloid precursor protein (APP) by presenilins (PSEN1 and PSEN2). Soluble Aβ oligomers can also cause synaptic dysfunction leading to neurodegeneration and cognitive disabilities. (Mucke, L., and Selkoe, D. J. (2012). Neurotoxicity of amyloid β-protein: synaptic and network dysfunction. Cold Spring Harb. Perspect. Med. 2, a006338, which is incorporated herein by reference). The neurofibrillary tangles in AD can include hyperphosphorylated tau protein, which is a microtubule associated protein in neurons. (Iqbal, K., et al. (2010). Tau in Alzheimer Disease and Related Tauopathies. Curr. Alzheimer Res. 7, 656-664, which is incorporated herein by reference). In AD, tau can be abnormally hyperphosphorylated and aggregate into filaments. (Grundke-Iqbal, I., et al. (1986). Abnormal phosphorylation of the microtubule-associated protein tau (tau) in Alzheimer cytoskeletal pathology. Proc. Natl. Acad. Sci. U.S.A 83, 4913-4917, which is incorporated herein by reference). Because of the strong evidence of involvement of Aβ in AD, several monoclonal antibody-based therapeutics were developed and tested to target the amyloid plaques. (van Dyck, C. H. (2018). Anti-Amyloid-β Monoclonal Antibodies for Alzheimer's Disease: Pitfalls and Promise. Biol. Psychiatry 83, 311-319, which is incorporated by reference in its entirety). Though studies in standard mammalian animal models showed that interventions that effectively prevent or removed Aβ accumulation in animal models, did not improve cognition in human clinical trials.

While about 5% of AD cases appear to have a genetic cause, 95% of the cases are sporadic or late-onset AD with unknown etiology. Less than 1% of AD cases are caused by genetic mutations in genes including APP, PSEN1 and PSEN2. Though several other genes were implicated in AD, one of the strongest genetic risk factors in AD is apoe. (Lambert, J.-C., et al. (2009). Genome-wide association study identifies variants at CLU and CR1 associated with Alzheimer's disease. Nat. Genet. 41, 1094-1099; Shen, L., and Jia, J. (2016). An Overview of Genome-Wide Association Studies in Alzheimer's Disease. Neurosci. Bull. 32, 183-190, each of which is incorporated herein by reference). A lipid/cholesterol carrier apolipoprotein E (APOE) is encoded by apoe. In humans, there are 3 major protein variants, termed APOE2, APOE3, and APOE4, that differ from each other only at two amino acid residues. (Mahley, R. W. (2016). Apolipoprotein E: from cardiovascular disease to neurodegenerative disorders. J. Mol. Med. Berl. Ger. 94, 739-746, which is incorporated herein by reference). People carrying polymorphism in apoe, specifically the apoe4 allele are significantly more likely develop AD, but also early-onset AD, compared to the people who carry either the apoe2 or apoe3 alleles. (Roses, A. D. (1996). Apolipoprotein E alleles as risk factors in Alzheimer's disease. Annu. Rev. Med. 47, 387-400; Strittmatter, W. J., and Roses, A. D. (1996). Apolipoprotein E and Alzheimer's disease. Annu. Rev. Neurosci. 19, 53-77, each of which is incorporated herein by reference). While APOE2 is thought to be the protective form of APOE, APOE4 is thought to be the "toxic" form. (Strittmatter and Roses, 1996, which is incorporated herein by reference). APOE4 exacerbates brain changes associated with AD including increased levels of amyloid deposits, brain dysfunction and neurodegeneration. (DiBattista, A. M., et al. (2016). Alzheimer's Disease Genetic Risk Factor APOE-ε4 Also Affects Normal Brain Function. Curr. Alzheimer Res. 13, 1200-1207, which is incorporated herein by reference). Despite the importance of APOE4 in AD, the molecular mechanisms of how APOE4 promotes AD pathogenesis is still not well-understood. (Kanekiyo, T., et al. (2014). ApoE and Aβ in Alzheimer's disease: accidental encounters or partners? Neuron 81, 740-754, which is incorporated by reference in its entirety). APOE4 is thought to contribute to AD pathogenesis via both loss-of-function and gain-of-function mechanisms. (DiBattista, 2016; Zepa, L., et al. (2011). ApoE4-Driven Accumulation of Intraneuronal Oligomerized Aβ42 following Activation of the Amyloid Cascade In Vivo Is Mediated by a Gain of Function. Int. J. Alzheimers Dis. 2011, each of which is incorporated herein by reference).

Earlier studies suggested that APOE isoforms binds and helps to clear Aβ. (Kim, J., et al. (2009). The role of apolipoprotein E in Alzheimer's disease. Neuron 63, 287-303, which is incorporated herein by reference). Compared to APOE2 and APOE3, APOE4 was suggested to be less efficient in clearing Aβ (Kim, 2009, which is incorporated herein by reference). However, recent studies suggest that APOE compete with Aβ for uptake through apoE receptors. (Verghese, P. B., et al. (2013). APOE influences amyloid-β (Aβ) clearance despite minimal APOE/Aβ association in physiological conditions. Proc. Natl. Acad. Sci. U.S.A 110, E1807-1816; Yajima, R., et al. (2015). APOE-isoform-dependent cellular uptake of amyloid-β is mediated by lipoprotein receptor LR11/SorLA. Biochem. Biophys. Res. Commun. 456, 482-488, each of which is incorporated herein by reference). While all the isoforms were able to compete for binding to APOE receptor, APOE4 expressing cells were less efficient in clearing Aβ. (Verghese, 2013, which is incorporated herein by reference).

Though, the role of APOE4 in Aβ brain pathology has been well-documented, the influence of APOE4 in tau pathology has been only recently explored. Using a tauopathy model that overexpress 1N4R human tau containing the P301S mutation, it was shown that ApoE4 exacerbates tau induced neuroinflammation and neurodegeneration phenotypes independent of Aβ pathology. (Shi, Y., et al. (2017). ApoE4 markedly exacerbates tau-mediated neurodegeneration in a mouse model of tauopathy. Nature 549, 523-527, which is incorporated herein by reference). The Tau P301S mutation was originally found in human cases with frontotemporal dementia and degeneration. (Bugiani, O., et al. (1999). Frontotemporal Dementia and Corticobasal Degeneration in a Family with a P301S Mutation in Tau. J. Neuropath. Exp. Neurol. 58, 667-677, which is incorporated herein by reference). Further, the tau P301S mutant proteins are more favorable substrates for phosphorylation compared to the wild-type tau. (Alonso, A. del C., et al. (2004). Promotion of hyperphosphorylation by frontotemporal dementia tau mutations. J. Biol. Chem. 279, 34873-34881, which is incorporated herein by reference). Interestingly, the neurofibrillary tangles found in AD are composed primarily of hyperphosphorylated tau. (Iqbal, 2010, which is incorporated herein by reference). Also, in frontotemporal dementia patients, the frequency of APOE4 allele is significantly higher (Stevens, M., et al. (1997). Apolipoprotein E gene and sporadic frontal lobe dementia. Neurology 48, 1526-1529, which is incorporated herein by reference) and APOE4 carriers also have increased disease severity (Agosta, F., et al. (2009). Apolipoprotein E ε4 is associated with disease-specific effects on brain atrophy in Alzheimer's disease and frontotemporal dementia. Proc. Natl. Acad. Sci. 106, 2018-2022; Engelborghs, S., et al. (2006). Dose dependent effect of APOE epsilon4 on behavioral symptoms in frontal lobe dementia. Neurobiol. Aging 27, 285-292, each of which is incorporated herein by reference). Despite the importance of APOE4 in AD, therapies targeting APOE4 is lacking. (Michaelson, D. M. (2014). APOE ε4: The most prevalent yet understudied risk factor for Alzheimer's disease. Alzheimers Dement. J. Alzheimers Assoc. 10, 861-868; Holtzman, D. M., et al. (2012). Apolipoprotein E and Apolipoprotein E Receptors: Normal Biology and Roles in Alzheimer Disease. Cold Spring Harb. Perspect. Med. 2, each of which is incorporated herein by reference). Moreover, despite being identified in more than half of all AD patients, ApoE4 carriers are often excluded in the clinical trials for AD because of the unpredictability of their response. (Qiu, W. Q., et al. (2013). Angiotensin converting enzyme inhibitors and the reduced risk of Alzheimer's disease in the absence of apolipoprotein E4 allele. J. Alzheimers Dis. JAD 37, 421-428; Sperling, R., et al. (2012). Amyloid-related imaging abnormalities in patients with Alzheimer's disease treated with bapineuzumab: a retrospective analysis. Lancet Neurol. 11, 241-249; Farlow, M. R., et al. (1998). Treatment outcome of tacrine therapy depends on apolipoprotein genotype and gender of the subjects with Alzheimer's disease. Neurology 50, 669-677; Risner, M. E., et al. (2006). Efficacy of rosiglitazone in a genetically defined population with mild-to-moderate Alzheimer's disease. Pharmacogenomics J. 6, 246-254; each of which is incorporated herein by reference).

Interestingly, although APOE4 is expressed in the brain, the peripheral tissue expression of APOE4 is high; this raises the possibility that peripheral APOE4 could contribute to AD pathogenesis. Apart from brain, APOE protein is synthesized primarily in the liver and is involved in lipid transport and cholesterol homeostasis. (Safieh, M., et al. (2019). ApoE4: an emerging therapeutic target for Alzheimer's disease. BMC Med. 17, which is incorporated herein by reference). Liver is the primary site which encounters not only the nutrients but also gut microbiome-derived small molecules or metabolites or toxins through the enterohepatic circulation. Thus, dysbiosis in the gut will have profound effect on the liver. One possibility is that AD might have a gut-origin: "microbiome-derived materials" might leak into the enterohepatic circulation and reaches the liver. From liver, the APOE4 might transport these "microbiome-derived materials" to brain where they could either seed amyloid deposits and/or increase neuroinflammation. Recent studies have suggested that the gut microbiome plays an important role in AD. Significant changes in the microbiome were observed in human AD patients compared to control populations. However, whether these changes are the cause or consequence of the disease is not known. Though many of the microbiome components are implicated in either susceptibility or pathogenesis of AD, the molecular mechanisms of such interactions remains unknown.

Example 2.2: APOE4 Enhances a Aβ-Induced Paralysis Phenotype

To test whether microbes modulate AD pathogenesis, transgenic C. elegans strains expressing human APOE4 were developed. These transgenic C. elegans strains expressed human APOE4 in the gut of C. elegans under the control of an intestinal promoter along with a signal sequence that allows the human APOE4 to be secreted out of the cell [e.g., mbEx2(pvha-6::ssapoe4)], or without a signal sequence [e.g., mbEx1(pvha-6::apoe4)]. In C. elegans, there is no liver and the gut perform all the functions that liver typically does. Animals were administered with the E. coli OP50 standard laboratory strain. Animals were monitored from day1 adulthood every alternative day until all were paralyzed. For each assay, at least 20 animals (as listed in TABLE 4) were recorded. Data from three independent trials was obtained. For each data point, mean±s.d is presented in the graph of FIG. 1. Transgenic animals expressing human APOE4 with or without the signal sequence did not show any apparent phenotypes (FIG. 1).

Expression of human Aβ1-42 in the C. elegans muscles has been reported to induce paralysis phenotype. (Link, C. D. (1995). Expression of human beta-amyloid peptide in transgenic Caenorhabditis elegans. Proc. Natl. Acad. Sci. U.S.A 92, 9368-9372, which is incorporated herein by reference). To determine whether human APOE4 modulates a paralysis phenotype induced by human Aβ1-42 in the muscles, animals listed in TABLE 4 were analyzed.

TABLE 4

| C. elegans | Expressed |
|---|---|
| mbEx1(pvha-6::apoe4) | APOE4 without signal sequence |
| mbEx2(pvha-6::ssapoe4) | APOE4 with signal sequence |
| dvIs2(punc-54::Abeta1-42) | Aβ1-42 |
| mbEx1(pvha-6::apoe4); dvIs2(punc-54::Abeta1-42) | APOE4 without signal sequence; Aβ1-42 |
| mbEx2(pvha-6::ssapoe4); dvIs2(punc-54::Abeta1-42) | APOE4 with signal sequence; Aβ1-42 |

Expression of APOE4 with a signal sequence enhanced the Aβ-induced paralysis phenotype. While ~40% of animals that expressed Aβ were paralyzed, >90% of animals that expressed both Aβ and APOE4 with a signal sequence were paralyzed by day 8 of adulthood (FIG. 1). However, the paralysis phenotype of animals that expressed Aβ and APOE4 without a signal sequence was similar to that of animals that expressed Aβ by itself (FIG. 1). In contrast, expressing APOE4 by itself, with or without the signal sequence, in the absence of Aβ expression did not induce paralysis phenotype adulthood (FIG. 1).

For the remainder of the studies described herein, a strain that expressed APOE4 with a signal sequence, which will be referred to ssApoE4, was analyzed.

Example 2.3: Aβ3-42 Conjugated to GFP and Human ssAPOE4 was Significantly Increased Expression of human Aβ$_{3-42}$ conjugated with GFP in C. elegans muscles has been reported to cause aggregate formation. (Link, C. D., Fonte, V., Roberts, C. M., Hiester, B., Silverman, M. A., and Stein, G. H. (2008). The beta amyloid peptide can act as a modular aggregation domain. Neurobiol. Dis. 32, 420-425, which is incorporated herein by reference). To determine whether expression of human ssApoE4 affects Aβ aggregate formation in C. elegans, animals that express human ssApoE4 along with human Aβ3-42 conjugated to GFP were generated. Animals listed in TABLE 5 below were administered with the *E. coli* OP50 standard laboratory strain.

TABLE 5

| C. elegans | Expressed |
|---|---|
| GFP::A-Beta (3-42) | Aβ3-42 |
| ssApoE4::GFP::A-Beta (3-42) | APOE4 with signal sequence; Aβ3-42 |

GFP aggregates in the anterior region of the animal were counted when the animals reached adulthood. For each assay, at least 17 animals were recorded. For each data point, mean±s.d is presented in the graph of FIG. 2. Compared to animals expressing Aβ3-42, animals expressing Aβ3-42 and ssApoE4 had significantly increased GFP aggregates as analyzed using Student's t-test, P<0.0001.

Figure 2:
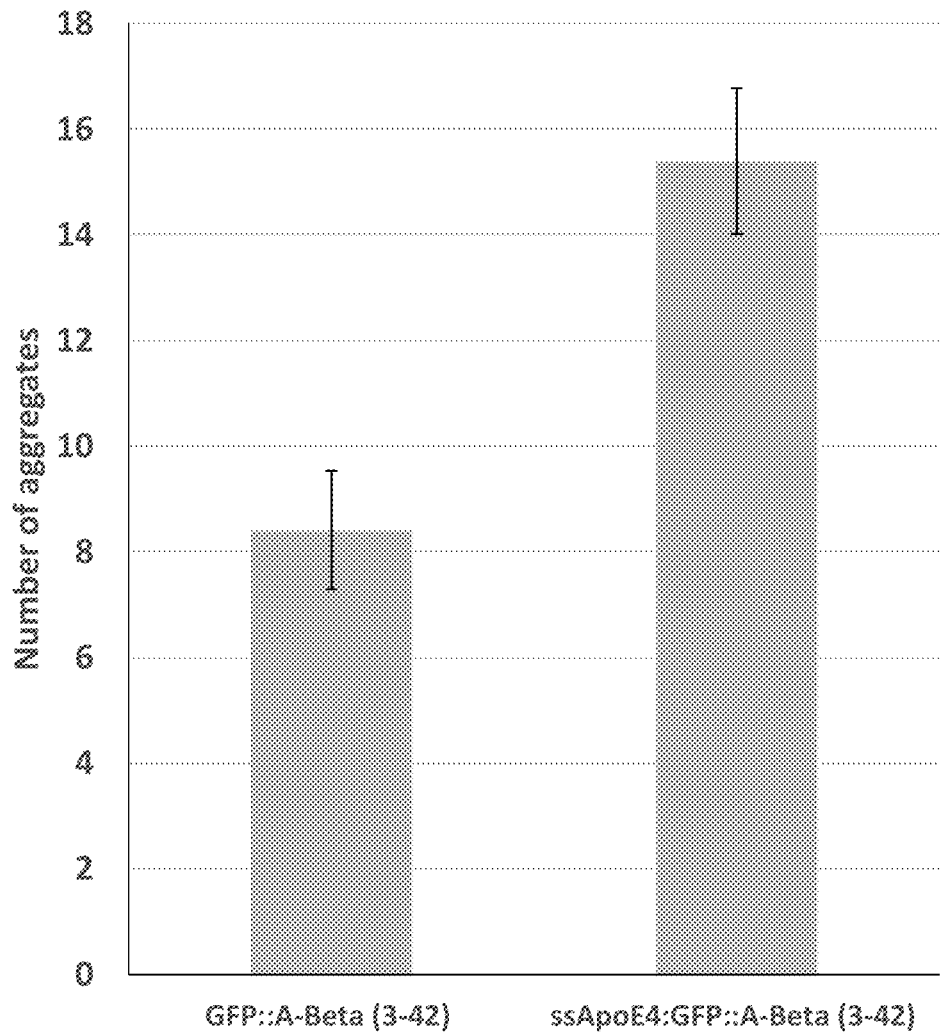
FIG. 2 shows data evidencing that expression of Aβ$_{3-42}$conjugated to green fluorescent protein (GFP) and human ssAPOE4 significantly increased the number of aggregates. C. elegans animals having the indicated genotypes were administered an E. coli OP50 standard laboratory strain. GFP aggregates in the anterior region of the animal were counted when the animals reached adulthood. For each assay, at least 17 animals were recorded. For each data point, mean±s.d is presented in a bar graph. Compared to animals expressing Aβ-42, animals expressing Aβ3-42 and ssApoE4 had significantly increased GFP aggregates as analyzed using Student's t-test, P<0.0001.

Compared to the number of aggregates in the anterior area of animals that expressed human $Aβ_{3-42}$ conjugated to GFP, the number of aggregates in animals that expressed both $Aβ_{3-42}$ conjugated to GFP and human ssApoE4 was significantly increased (FIG. 2). Interestingly, Aβ deposition in AD patients has been reported to be higher in APOE4 carriers in comparison with non-carriers. (Dorey, E., Chang, N., Liu, Q. Y., Yang, Z., and Zhang, W. (2014). Apolipoprotein E, amyloid-beta, and neuroinflammation in Alzheimer's disease. Neurosci. Bull. 30, 317-330, which is incorporated herein by reference).

Example 2.4: UbV-GFP is Stabilized in Animals Expressing Both Human ssAPOE4 and Human Tau352 (PHP)

Hyperphosphoryated tau has been reported to be associated with AD. Expression of pseudohyperphosphorylated tau, which mimics AD-relevant modification, was further reported to induce progressive age-dependent locomotion defects in *C. elegans*. (Brandt, R., Gergou, A., Wacker, I., Fath, T., and Hutter, H. (2009). A *Caenorhabditis elegans* model of tau hyperphosphorylation: induction of developmental defects by transgenic overexpression of Alzheimer's disease-like modified tau. Neurobiol. Aging 30, 22-33, which is incorporated herein by reference).

To analyze whether ssAPOE4 modulates tau-induced defects in *C. elegans*, a transgenic strain that expressed pseudohyperphosphorylated human tau and human ssA-POE4 was generated. Animals of the appropriate genotypes were administered with the *E. coli* op50 standard laboratory strain. No apparent differences locomotion was observed in between the strain that expressed pseudohyperphosphorylated human tau and human ssAPOE4 compared to the strain that expressed the pseudohyperphosphorylated human tau strain alone (data not shown).

Proper proteasomal function is important for cellular function and previous studies in the field have shown that proteasomal function is impaired in human AD (Bonet-Costa, V., et al. (2016). The Proteasome and Oxidative Stress in Alzheimer's Disease. Antioxid. Redox Signal. 25, 886-901; Upadhya, S. C., and Hegde, A. N. (2007). Role of the ubiquitin proteasome system in Alzheimer's disease. BMC Biochem. 8, S12; Oddo, S. (2008). The ubiquitin-proteasome system in Alzheimer's disease. J. Cell. Mol. Med. 12, 363-373; Zheng, Q., et al. (2016). Dysregulation of Ubiquitin-Proteasome System in Neurodegenerative Diseases. Front. Aging Neurosci. 8, each of which is incorporated herein by reference). To determine whether ssApoE4 expression affects proteasomal function, animals that carry human ssApoE4 and a marker for impaired proteasomal function were generated (TABLE 6). The proteasomal dysfunction marker consists of a noncleavable ubiquitin that is N-terminally fused to GFP (UbV-GFP).

TABLE 6

| C. elegans | Expressed |
|---|---|
| UbV-GFP | ubiquitin N-terminally fused to GFP |
| ssapoe4; UbV-GFP | APOE4 with signal sequence; ubiquitin N-terminally fused to GFP |
| Tau352(PHP);UbV-GFP | Pseudohyperphosphorylated tau protein; ubiquitin N-terminally fused to GFP |
| ssapoe4; Tau352(PHP); UbV-GFP | APOE4 with signal sequence; Pseudohyperphosphorylated tau protein; ubiquitin N-terminally fused to GFP |

Figure 3:
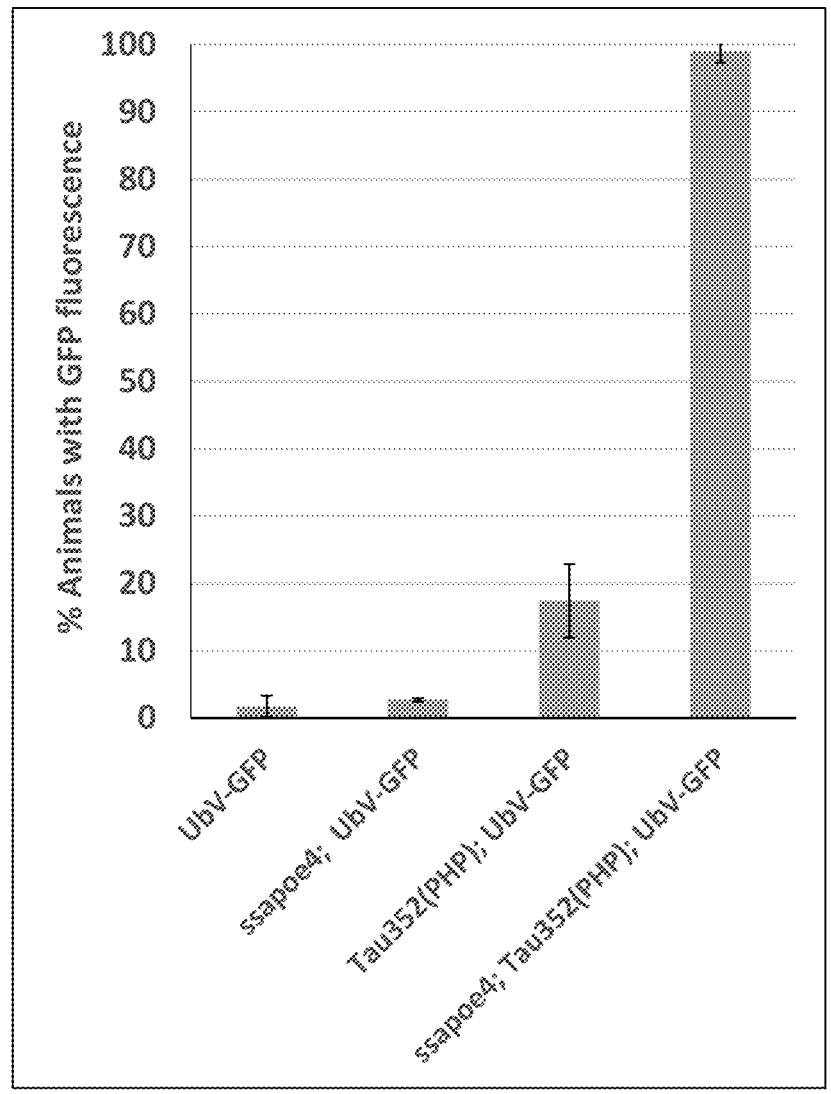
FIG. 3 shows data evidencing that UbV-GFP is stabilized in animals expressing both human ssAPOE4 and human tau352(PHP). C. elegans animals having the indicated genotypes were administered with the E. coli OP50 standard laboratory strain. The number of animals expressing GFP in the gut were counted when the animals reached adulthood. For each assay, at least 30 animals were recorded. Data from three independent trials are presented in a bar graph. For each data point, mean±s.d is presented in the graph. Compared to animals that expressed tau352(PHP), animals expressing ssAPOE4 and tau352(PHP) had significantly increased UbV-GFP expression as analyzed using Student's t-test, P<0.0001.

The number of animals expressing GFP in the gut were counted when the animals reached adulthood. For each assay, at least 30 animals were recorded. Data from three independent trials are presented in (FIG. 3). For each data point, mean±s.d is presented in the graph. Compared to animals that expressed tau352(PHP), animals expressing ssAPOE4 and tau352(PHP) had significantly increased UbV-GFP expression, as analyzed using Student's t-test, P<0.0001.

Generally, UbV-GFP undergoes proteasomal-dependent degradation, while impaired proteostasis causes stabilization of the GFP (see, e.g., FIG. 3). Minimal or no GFP expression was observed in animals expressing human ssApoE4; however, the UbV-GFP was stabilized in animals expressing both human ssApoE4 and human pseudohyperphosphorylated human tau (FIG. 3). Pseudohyperphosphorylated human tau expression itself did not induce proteasomal stress (FIG. 3). This result suggested that expression of human ssApoE4 and human pseudohyperphosphorylated human tau induces proteasomal stress.

Hyperphosphorylated Tau has previously been reported to be resistant to proteasomal degradation (Poppek, D., Keck, S., Ermak, G., Jung, T., Stolzing, A., Ullrich, O., Davies, K. J. A., and Grune, T. (2006). Phosphorylation inhibits turnover of the tau protein by the proteasome: influence of RCAN1 and oxidative stress. Biochem. J. 400, 511-520, which is incorporated herein by reference) and tau phosphorylation was reported to modulate proteasomal activity (Ren, Q.-G., Liao, X.-M., Chen, X.-Q., Liu, G.-P., and Wang, J.-Z. (2007). Effects of tau phosphorylation on proteasome activity. FEBS Lett. 581, 1521-1528; Johnson, G. V. W. (2006). Tau phosphorylation and proteolysis: insights and perspectives. J. Alzheimers Dis. JAD 9, 243-250, which is incorporated herein by reference). In the *C. elegans* transgenic strain, human pseudohyperphosphorylated human tau was expressed in the neurons, while human ssApoE4 was expressed under the control of intestinal promoter along with signal sequences, which allowed it be secreted out of the cell. The induction of UbV-GFP was primarily observed in the intestine of the animals (not shown). The intestine is large prominent tissue in *C. elegans*, which may mask the induction of UbV-GFP in other tissues. However, induction of UbV-GFP in the intestine provided an easy visual screening for interventions that might modify the proteasomal function.

Example 2.5: Microbial Strains Affect Aβ Paralysis

Animals of the appropriate genotypes were administered with either *E. coli* OP50 standard laboratory strain or individual microbiome strains. Number of paralyzed animals were recorded on day 4 of adulthood. Data from three independent trials are presented. For each data point, mean±s.d is presented in the graph. See Table 1 below for the raw data with number of animals analyzed for each condition.

Figure 4:
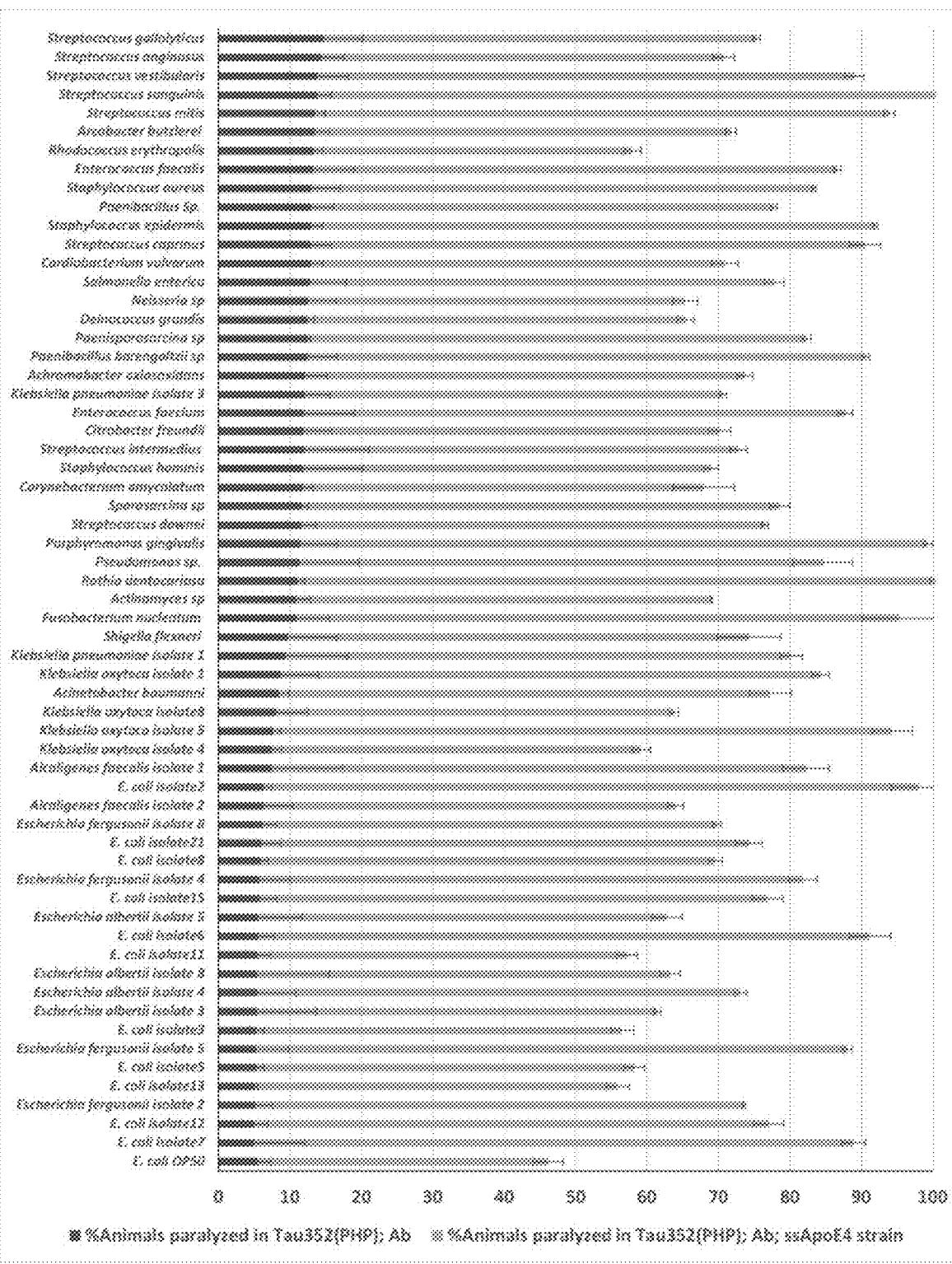
FIG. 4 includes data evidencing that certain microbial strains of a microbiome increase Aβ mediated paralysis. C. elegans animals having the indicated genotypes were administered with either E. coli OP50 standard laboratory strain or individual microbiome strains. Number of paralyzed animals were recorded on day 4 of adulthood. Data from three independent trials are presented in a bar graph. For each data point, mean±s.d is presented in the graph. Table 1 includes the raw data with number of animals analyzed for each condition.

To facilitate rapid screening of a microbiome for modulators, a novel transgenic *C. elegans* strain that expresses human ssApoE4, human Aβ1-42, human pseudophosphorylated tau and UbV-GFP proteasomal marker was generated. This transgenic strain can be employed for not only identifying interventions that suppress paralysis, but also for agents that improve proteasomal function. Further, this model could be used for finding parameters or features of a biological pathway affect (enhance or decrease) paralysis. Parameters or features could be small molecules, metabolites, nucleic acids, proteins, lipids, or even microbiome components. Approximately 1400 individual microbial strains from a human microbiome were administered to animals carrying human ssApoE4, human Aβ1-42, human pseudophosphorylated tau and UbV-GFP proteasomal marker. A degree of paralysis was observed. A group of microbial populations were found to enhance a paralysis phenotype of animals expressing human ssApoE4, human Aβ1-42, human pseudophosphorylated tau and UbV-GFP proteasomal marker (Table 7; FIG. 4). Enhancement of paralysis was dependent on the presence of ssAPOE4 because administration of many of these bacteria to animals that express human Aβ1-42, human pseudophosphorylated tau and UbV-GFP proteasomal marker did not enhance the paralysis phenotype (Table 7; FIG. 4).

TABLE 7

| Microbial isolate | % animal paralyzed (n) in strain expressing ssAPOE4, Tau352(PHP) and Aβ | % animals paralyzed (n) in strain expressing Tau352(PHP) and Aβ |
|---|---|---|
| *E. coli* OP50 | 40.6 ± 1.8 (305) | 5.5 ± 2.1 (288) |
| *E. coli* isolate 2 | 91.6 ± 1.1 (297) | 6.3 ± 3.7 (298) |
| *E. coli* isolate 6 | 85.6 ± 2.1 (298) | 5.6 ± 2.9 (305) |
| *E. coli* isolate 7 | 83.9 ± 7.1 (299) | 5.0 ± 1.7 (301) |
| *E. coli* isolate 3 | 51.2 ± 1.1 (299) | 5.4 ± 1.6 (299) |
| *E. coli* isolate 5 | 52.9 ± 1.1 (295) | 5.3 ± 1.5 (300) |
| *E. coli* isolate 12 | 71.9 ± 1.8 (281) | 5.1 ± 2.1 (297) |
| *E. coli* isolate 15 | 71.1 ± 2.4 (301) | 5.7 ± 2.2 (297) |
| *E. coli* isolate 8 | 63.6 ± 1.0 (299) | 6.0 ± 1.0 (301) |
| *E. coli* isolate 21 | 68.2 ± 2.7 (285) | 6.0 ± 1.9 (300) |
| *E. coli* isolate 13 | 50.7 ± 0.3 (302) | 5.2 ± 1.6 (286) |
| *E. coli* isolate 11 | 51.7 ± 1.8 (302) | 5.5 ± 1.4 (289) |
| *Escherichia fergusonii* isolate 2 | 68.3 ± 2.4 (297) | 5.2 ± 0.2 (290) |
| *Escherichia fergusonii* isolate 4 | 76.0 ± 4.2 (304) | 5.8 ± 2.0 (292) |
| *Escherichia fergusonii* isolate 5 | 82.7 ± 4.4 (304) | 5.4 ± 0.7 (299) |
| *Escherichia fergusonii* isolate 8 | 63.5 ± 1.8 (296) | 6.3 ± 0.6 (304) |
| *Escherichia albertii* isolate 5 | 57.1 ± 6.1 (291) | 5.6 ± 2.1 (302) |
| *Escherichia albertii* isolate 3 | 56.0 ± 8.1 (300) | 5.5 ± 0.5 (292) |
| *Escherichia albertii* isolate 8 | 57.7 ± 10.0 (299) | 5.5 ± 1.4 (290) |
| *Escherichia albertii* isolate 4 | 67.6 ± 5.3 (297) | 5.5 ± 0.8 (293) |
| *Klebsiella oxytoca* isolate 1 | 75.5 ± 5.3 (295) | 8.7 ± 1.2 (299) |
| *Klebsiella oxytoca* isolate 8 | 55.6 ± 4.3 (300) | 8.1 ± 0.6 (308) |
| *Klebsiella oxytoca* isolate 4 | 51.7 ± 1.3 (302) | 7.5 ± 1.3 (305) |
| *Klebsiella oxytoca* isolate 5 | 86.7 ± 1.2 (293) | 7.6 ± 2.8 (284) |
| *Klebsiella pneumoniae* isolate 1 | 70.8 ± 8.6 (300) | 9.4 ± 1.6 (299) |
| *Klebsiella pneumoniae* isolate 3 | 58.4 ± 3.4 (303) | 12.2 ± 0.5 (296) |
| *Streptococcus downei* | 64.8 ± 2.0 (301) | 11.6 ± 0.4 (301) |
| *Streptococcus sanguinis* | 90.3 ± 2.0 (299) | 13.8 ± 1.2 (297) |
| *Streptococcus vestibularis* | 75.1 ± 4.4 (297) | 13.9 ± 1.4 (297) |
| *Streptococcus mitis* | 80.4 ± 1.4 (305) | 13.5 ± 0.7 (303) |
| *Streptococcus gallolyticus* | 60.5 ± 5.4 (296) | 14.7 ± 0.5 (305) |
| *Streptococcus anginosus* | 56.3 ± 3.1 (297) | 14.4 ± 1.5 (300) |
| *Streptococcus.caprinus* | 77.5 ± 2.9 (298) | 12.9 ± 2.2 (302) |
| *Streptococcus intermedius* | 60.8 ± 9.1 (303) | 11.9 ± 1.2 (302) |
| *Staphylococcus aureus* | 70.3 ± 4.0 (303) | 13.0 ± 0.3 (307) |
| *Staphylococcus epidermis* | 79.0 ± 1.6 (300) | 13.0 ± 0.3 (301) |
| *Staphylococcus hominis* | 57.1 ± 8.2 (305) | 11.9 ± 1.0 (287) |
| *Paenisporosarcina sp* | 69.8 ± 0.4 (288) | 12.5 ± 0.6 (296) |
| *Paenibacillus sp.* | 78.1 ± 4.1 (309) | 12.5 ± 0.5 (305) |
| *Sporosarcina Sp.* | 66.8 ± 0.8 (301) | 11.7 ± 1.4 (308) |
| *Paenibacillus Sp.* | 64.7 ± 3.1 (287) | 13.0 ± 0.4 (293) |
| *Alcaligenes faecalis* isolate 1 | 74.7 ± 9.9 (297) | 7.5 ± 3.2 (294) |
| *Alcaligenes faecalis* isolate 2 | 57.7 ± 4.1 (297) | 6.3 ± 1.1 (285) |
| *Enterococcus faecium* | 75.7 ± 6.9 (296) | 12.0 ± 1.0 (300) |
| *Enterococcus faecalis* | 73.3 ± 5.6 (304) | 13.3 ± 0.5 (309) |

TABLE 7-continued

| Microbial isolate | % animal paralyzed (n) in strain expressing ssAPOE4, Tau352(PHP) and Aβ | % animals paralyzed (n) in strain expressing Tau352(PHP) and Aβ |
|---|---|---|
| *Deinococcus grandis* | 52.9 ± 0.9 (310) | 12.5 ± 1.2 (312) |
| *Neisseria sp* | 52.7 ± 3.9 (302) | 12.6 ± 1.8 (302) |
| *Rhodococcus erythropolis* | 44.6 ± 1.3 (316) | 13.3 ± 1.2 (316) |
| *Corynebacterium amycolatum* | 56.2 ± 1.5 (301) | 11.7 ± 4.3 (292) |
| *Actinomyces sp* | 58.0 ± 2.0 (300) | 11.0 ± 0.1 (301) |
| *Rothia dentocariosa* | 92.3 ± 1.1 (299) | 11.0 ± 3.7 (300) |
| *Arcobacter butzlerei* | 58.3 ± 2.1 (292) | 13.5 ± 0.7 (304) |
| *Citrobacter freundii* | 58.2 ± 3.9 (301) | 11.9 ± 1.5 (301) |
| *Acinetobacter baumanni* | 68.7 ± 1.4 (310) | 8.5 ± 2.1 (299) |
| *Porphyromonas gingivalis* | 87.9 ± 5.1 (297) | 11.4 ± 0.6 (298) |
| *Fusobacterium nucleatum* | 84.4 ± 4.6 (300) | 10.9 ± 5.2 (302) |
| *Salmonella enterica* | 64.9 ± 5.0 (291) | 12.9 ± 1.4 (295) |
| *Shigella flexneri* | 64.5 ± 6.7 (303) | 9.8 ± 4.4 (306) |
| *Pseudomonas sp.* | 73.3 ± 8.3 (292) | 11.3 ± 4.2 (292) |
| *Cardiobacterium vulvarum* | 57.9 ± 1.7 (302) | 12.9 ± 1.9 (302) |
| *Achromabacter oxlosoxidans* | 61.5 ± 3.0 (296) | 12.2 ± 1.1 (296) |

Example 2.6: Microbial Strains Modulate Aβ3-42::GFP Aggregation

Included in microbial populations that were observed to enhance paralysis in *C. elegans* animals expressing human ssApoE4, human Aβ1-42, human pseudophosphorylated tau and UbV-GFP proteasomal marker was *Porphyromonas gingivalis* (Table 1). *P. gingivalis* was identified in AD patient brain and was implicated in neurotoxic tau and amyloid deposition. (Dominy, S. S., et al. (2019). *Porphyromonas gingivalis* in Alzheimer's disease brains: Evidence for disease causation and treatment with small-molecule inhibitors. Sci. Adv. 5, which is incorporated herein by reference). Further, *P. gingivalis* has been reported to increase ubiquitin load, suggesting a disruption of proteasomal function. (Dominy et al., 2019, which is incorporated herein by reference). Oral administration of *P. gingivalis* was previously shown to be sufficient to induce brain infection and induction of Aβ deposits (Dominy et al., 2019, which is incorporated herein by reference).

Animals were administered with either *E. coli* OP50 standard laboratory strain or individual microbiome strains. GFP aggregates in the anterior region of the animal were counted when the animals reached adulthood. GFP aggregates in three animals were counted for each condition. For each data point, mean±s.d is presented in the graph.

Figure 5:
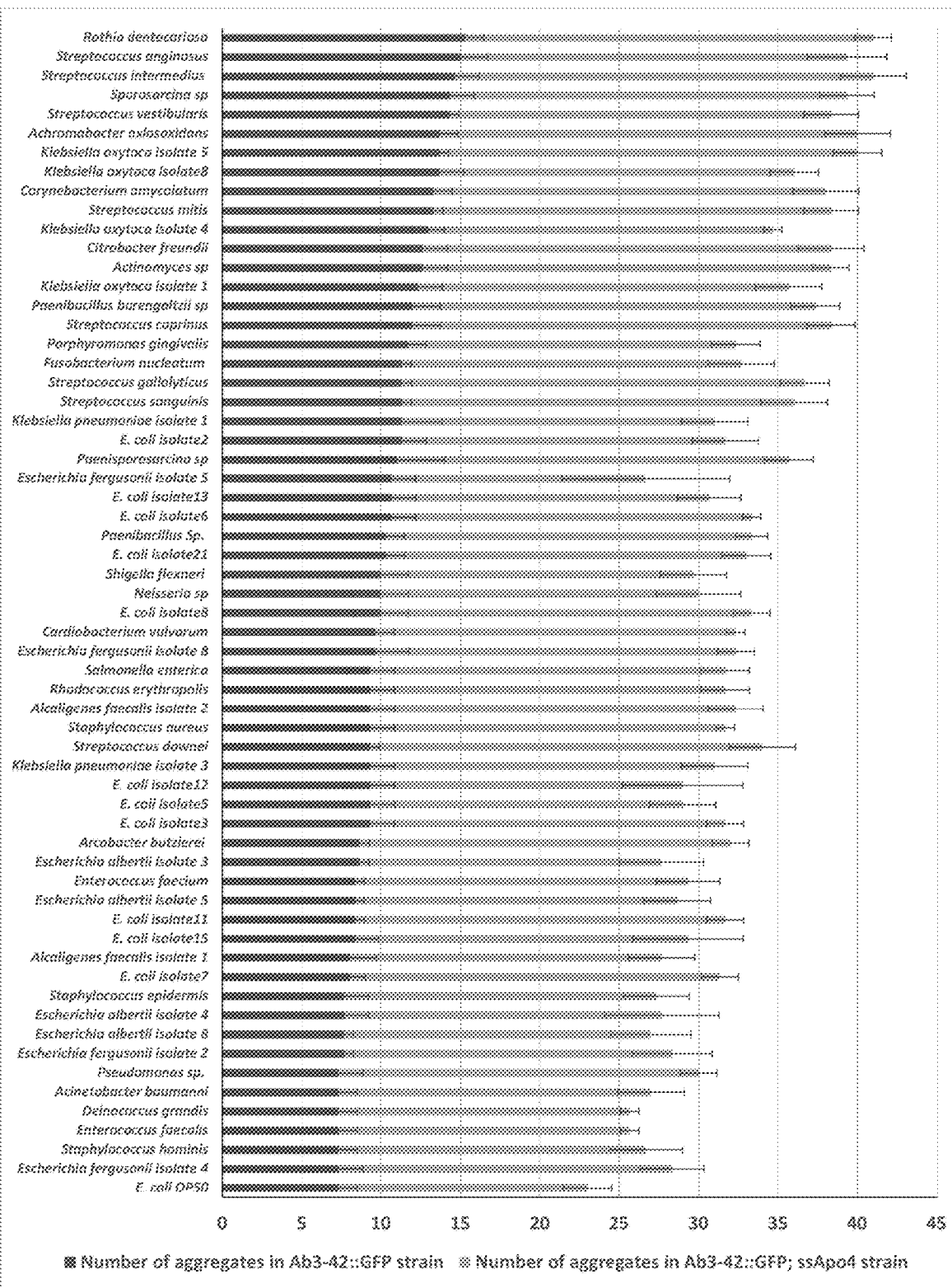
FIG. 5 includes data evidencing certain microbial strains of a microbiome modulate Aβ3-42::GFP aggregation. C. elegans animals having the indicated genotypes were administered with either E. coli op50 standard laboratory strain or individual microbiome strains. The number of GFP aggregates in the anterior region of the animal were counted when the animals reached adulthood. GFP aggregates in three animals were counted for each condition. For each data point, mean±s.d is presented in the graph.

Administration of *P. gingivalis* induced increased Aβ$_{3-42}$::GFP aggregates; however, the Aβ$_{3-42}$::GFP aggregates were increased significantly higher in animals expressing human ssApoE4 and Aβ$_{3-42}$::GFP together (FIG. 5). This result suggested that the ssApoE4 genotype has a deleterious effect in increasing the incidence AD associated symptoms. Thus, identification of a known microbial population that was previously implicated in AD validates that a transgenic human ssApoE4, pseudophosphorylated tau and Aβ expressing *C. elegans* platform assay. The results confirm that other microbial populations discovered might be factors that affect AD risk in humans.

Interestingly, several *E. coli* isolates were found that increased a paralysis phenotype, as well as caused increased Aβ$_{3-42}$::GFP aggregates in a ssAPOE4 dependent fashion (TABLE 7; FIG. 4; FIG. 5). This is interesting at least because *C. elegans* are fed on a standard non-pathogenic *E. coli* OP50 strain in the lab. Previous studies have shown that gram-negative bacterial molecules especially from *E. coli* are associated with AD neuropathology. (Zhan, X., Stamova, B., Jin, L.-W., DeCarli, C., Phinney, B., and Sharp, F. R. (2016). Gram-negative bacterial molecules associate with Alzheimer disease pathology. Neurology 87, 2324-2332, which is incorporated herein by reference). It is possible that these factors are not expressed or weakly expressed in *E. coli* OP50 strain or this could suggest strain-specific difference. The 11 strains of *E. coli* tested were classified into strains that had either mild, moderate or severe effect on the paralysis (TABLE 7; FIG. 4) or Aβ$_{3-42}$::GFP aggregate phenotype (FIG. 5). These data suggest that strain specific differences in microbial populations could contribute the occurrence or severity of AD.

*E. fergusonii* and *E. albertii* also showed similar trends to that of *E. coli*. While some isolates of *E. fergusonii* and *E. albertii* increased the paralysis phenotype, others strains had either mild or moderate effects (TABLE 7). This peculiar effect on paralysis was also observed in isolates of *Klebsiella oxytoca*, *Klebsiella pnuemoniae* and *Alcaligenes faecalis*. This might be a general tendency for other microbial populations as well, but because of the number of strains analyzed, this feature might be missed. Thus, among other things, the present disclosure teaches that individual strains of a particular microbe can have differential effects on biological phenotype(s), specifically including disease-associated phenotype(s). In some embodiments, the present disclosure provides technologies for identifying and/or characterizing particular strains, and/or components or combinations thereof, which may achieve a particular impact on a biological phenotype.

Further, microbiome samples from apparently healthy donors were analyzed. It is possible that AD patient microbiome samples might produce a better trend in identifying strains that might have deleterious effects. However, using this *C. elegans* characterization system, a patient microbiome could be assessed for increased or decreased presence of microbial strains that are associated with or, alternatively affect, disease. Though metagenomic sequencing of patient population could identify the diversity of microbial species present in a particular patient or patient population, these methods cannot identify strain-level differences in patient samples compared to healthy population. The present system fills this gap in identifying strain-level differences in patient(s) and/or patient population(s), which may be important for a number of diseases or conditions, including AD. Thus, this platform could serve us a potential early diagnostic disease predictor. Thus, among other things, the present disclosure provides technologies for defining, assessing, and/or detecting, microbes, and/or components or combinations thereof (i.e., microbial signature(s)), that may be associated with a particular disease states; in some embodiments, such microbial signatures can be detected in patient sample(s) and, for example, may be useful to diagnose a disease state, to monitor impact of a particular therapy with respect to such disease state, etc.

Example 2.7: Exemplary Microbial Strains that Affect ATP Production

The Neuro2A cell line was purchased from ATCC and cultured in EMEM media supplemented with 10% FBS, and 1% L-glutamine. Cells were maintained at 37° C./5% $CO_2$ incubators. All experiments were carried out using only passage 3-7 cells. Neuro2A cells ($5 \times 10^4$ cells per well) were plated onto a 96-well white-walled plate (Corning) and incubated overnight at 37° C./5% $CO_2$. Each of the 10 bacteria or a combination of all bacteria (CT10) were grown in the following media: Reinforced Clostridial Broth, Peptone Yeast extract Glucose broth, MRS broth and Tryptic Soy Broth. The bacteria were resuspended to $10^8$ CFU in PBS and stored at −80° C. $10^8$ CFU of each microbe (referred as samples) was added to 6 wells. The combination of all bacteria (CT10) was added to 6 wells at $10^9$ CFU (i.e., $10^8$ CFU of each bacteria). For the control wells, PBS with no bacteria were added. After 16 hours of incubation at 37° C./5% $CO_2$, 2 μM of Human Amyloid β1-42 was added to all the wells except for control untreated wells. The cells were incubated for 24 hours at 37° C./5% $CO_2$. The cells were washed with PBS three-times and 0.05 ml of Promega CellTiter-Glo and plate was incubated at room temperature shielded from light for 1 hour. The luminescence was measured using a microplate reader (Promega discoverer, Promega Corp), indicating the ATP levels. The ATP levels were normalized to protein content, as measured by the Bradford Protein Assay kit (ThermoFisher Scientific). 10 of samples was added to 150 μl of Bradford reagent in clear 96-well plates in duplicates and incubated for 5 min in dark at RT and the absorbance was measured at 600 nm using a microplate reader (Promega Discoverer, Promega Corp.). The normalized luminescence was calculated by dividing the luminescence value by OD protein absorbance value. The average of the triplicate wells for each condition was calculated % ATP compared to the control was calculated.

Figure 6:
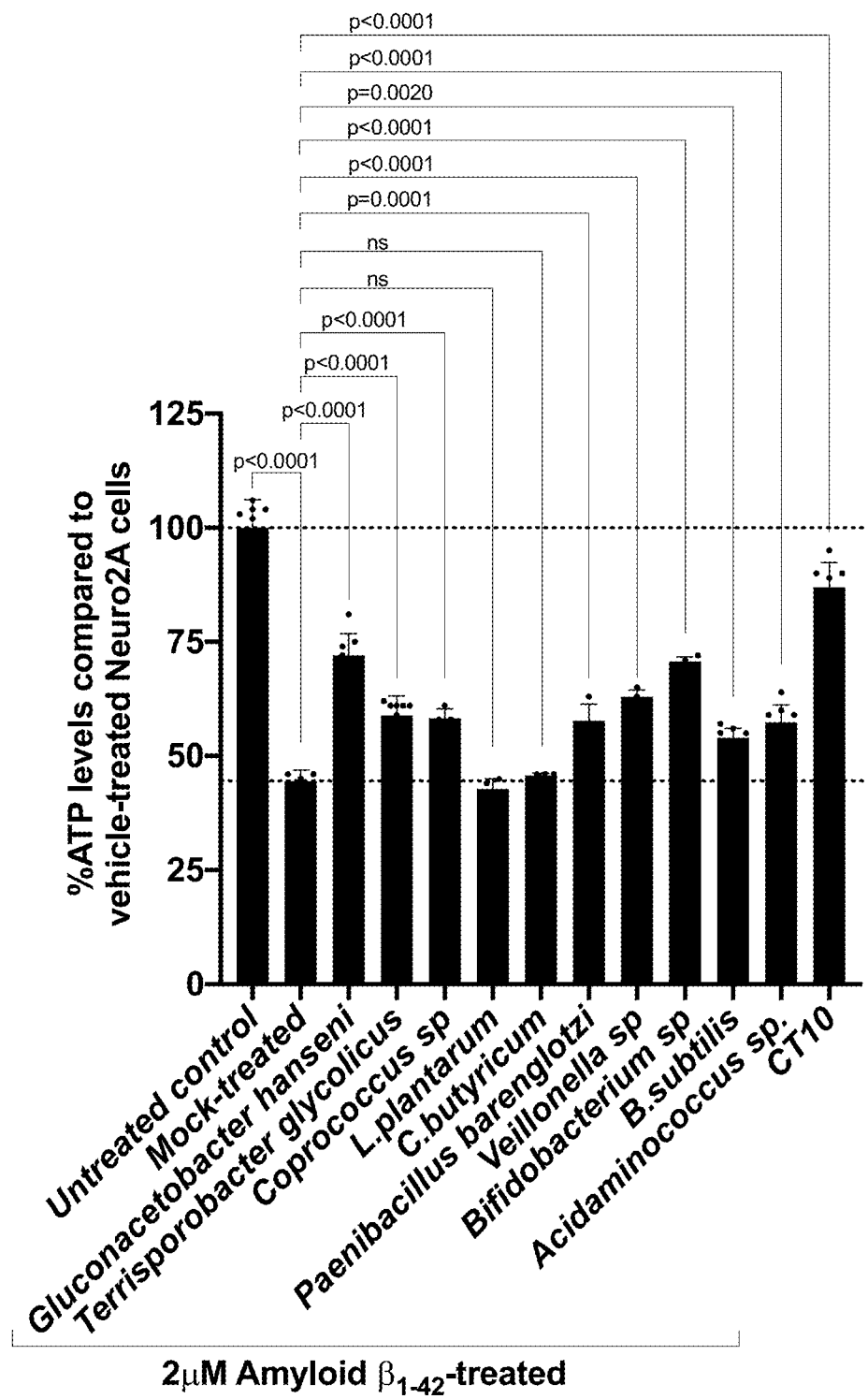
FIG. 6 includes data showing that certain microbial strains altered ATP production. Neuro2A cells were either mock-treated or treated with $10^8$ CFU of each bacterium or a combination of all bacteria (CT10) for 16 hours. 2 µM of Human Amyloid $β_{1-42}$ was added to all the wells except for the untreated wells. Cells were incubated for 24 hours and ATP levels were measured and normalized. The percent ATP was calculated according to the following formula: % ATP= [(sample normalized luminescence value/control normalized luminescence)*100].

As shown in FIG. 6, treating Neuro2A cells with 2 μM of Human Amyloid $β_{1-42}$ ("Mock-treated") caused significant decrease in ATP production. While treatment of Neuro2A cells with *Gluconacetobacter hansenii, Terrisporobacter glycolicus, Coprococcus* sp. or *Acidaminococcus* sp. resulted in significant increase in ATP production compared to the Mock-treated cells, a combination of all the bacteria together (CT-10) resulted in further significant increase in the ATP production in the presence of Human Amyloid $β_{1-42}$.

TABLE 8

Exemplary Microbial Strains Found in Human Gut Microbiome

| | |
|---|---|
| *Bacteroides pectinophilus* | *Exiguobacterium mexicanum* |
| *Acetobacter sp* | *Faecalibacterium prausnitzii* |
| *Acetobacterium tundrae* | *Faecalitalea cylindroides* |
| *Achromobacter aegrifaciens* | *Finegoldia magna* |
| *Achromobacter insuavis* | *Flavonifractor plautii* |
| *Achromobacter piechaudii* | *Flintibacter butyricus* |
| *Achromobacter xylosoxidans* | *Fusicatenibacter saccharivorans* |
| *Acidaminococcus fermentans* | *Fusobacterium gonidiaformans* |
| *Acidaminococcus intestini* | *Fusobacterium mortiferum* |
| *Acinetobacter baumannii* | *Fusobacterium nucleatum* |
| *Acinetobacter junii* | *Fusobacterium ulcerans* |
| *Actinomyces sp.* | *Fusobacterium varium* |
| *Agathobacter rectalis* | *Gardnerella vaginalis* |
| *Agathobaculum butyriciproducens* | *Gemella haemolysans* |
| *Aggregatibacter segnis* | *Gemella sanguinis* |
| *Akkermansia muciniphila* | *Gemmiger formicilis* |
| *Alistipes finegoldii* | *Gluconacetobacter sp* |
| *Alistipes indistinctus* | *Gluconobacter sp* |
| *Alistipes onderdonkii* | *Gordonibacter pamelaeae* |
| *Alistipes putredinis* | *Granulicatella adiacens* |
| *Alistipes shahii* | *Grimontia hollisae* |
| *Allisonella histaminiformans* | *Haemophilus parainfluenzae* |
| *Anaerobaculum hydrogeniformans* | *Harryflintia acetispora* |
| *Anaerococcus hydrogenalis* | *Helicobacter bilis* |
| Anaerococcus *octavius* | *Helicobacter bizzozeronii* |
| *Anaerococcus prevotii* | *Helicobacter canadensis* |
| *Anaerococcus tetradius* | *Helicobacter cinaedi* |
| *Anaerococcus vaginalis* | *Helicobacter pullorum* |
| *Anaerofilum agile* | *Helicobacter pylori* |
| *Anaerofustis stercorihominis* | *Helicobacter winghamensis* |
| *Anaerosporobacter mobilis* | *Holdemanella biformis* |
| *Anaerostipes caccae* | *Holdemania filiformis* |
| *Anaerostipes hadrus* | *Holdemania massiliensis* |
| *Anaerostipes rhamnosivorans* | *Hungatella effluvii* |
| *Anaerotruncus colihominis* | *Hungatella hathewayi* |
| *Anaerovorax odorimutans* | *Intestinimonas butyriciproducens* |
| *Arcobacter butzleri* | *Kineothrix alysoides* |
| *Asaccharobacter celatus* | *Kingella oralis* |
| *Atopobium parvulum* | *Klebsiella pneumoniae* |
| *Atopobium vaginae* | *Klebsiella pneumoniae subsp. ozaenae* |
| *Bacillus cereus* | *Klebsiella pneumoniae subsp. pneumoniae* |

TABLE 8-continued

Exemplary Microbial Strains Found in Human Gut Microbiome

| | |
|---|---|
| *Bacillus coagulans* | *Klebsiella pneumoniae* subsp. *rhinoscleromatis* |
| *Bacillus licheniformis* | *Klebsiella quasipneumoniae* subsp. *quasipneumoniae* |
| *Bacillus pseudomycoides* | *Klebsiella singaporensis* |
| *Bacillus sonorensis* | *Klebsiella variicola* |
| *Bacillus toyonensis* | *Lachnobacterium bovis* |
| *Bacillus wiedmannii* | *Lachnospira multipara* |
| *Bacteroides caccae* | *Lachnospira pectinoschiza* |
| *Bacteroides cellulosilyticus* | *Lactobacillus acidophilus* |
| *Bacteroides clarus* | *Lactobacillus amylolyticus* |
| *Bacteroides coprocola* | *Lactobacillus amylovorus* |
| *Bacteroides coprophilus* | *Lactobacillus antri* |
| *Bacteroides dorei* | *Lactobacillus brevis* subsp. *Gravesensis* |
| *Bacteroides eggerthii* | *Lactobacillus buchneri* |
| *Bacteroides faecis* | *Lactobacillus casei* |
| *Bacteroides finegoldii* | *Lactobacillus coryniformis* subsp. *Coryniformis* |
| *Bacteroides fluxus* | *Lactobacillus crispatus* |
| *Bacteroides fragilis* | *Lactobacillus delbrueckii* subsp. *Bulgaricus* |
| *Bacteroides intestinalis* | *Lactobacillus delbrueckii* subsp. *indicus* |
| *Bacteroides massiliensis* | *Lactobacillus delbrueckii* subsp. *Lactis* |
| *Bacteroides nordii* | *Lactobacillus fermentum* |
| *Bacteroides oleiciplenus* | *Lactobacillus fructivorans* |
| *Bacteroides ovatus* | *Lactobacillus gasseri* |
| *Bacteroides plebeius* | *Lactobacillus helveticus* |
| *Bacteroides salanitronis* | *Lactobacillus hilgardii* |
| *Bacteroides salyersiae* | *Lactobacillus iners* |
| *Bacteroides stercoris* | *Lactobacillus jensenii* |
| *Bacteroides thetaiotaomicron* | *Lactobacillus johnsonii* |
| *Bacteroides uniformis* | *Lactobacillus mucosae* |
| *Bacteroides vulgatus* | *Lactobacillus oris* |
| *Bacteroides xylanisolvens* | *Lactobacillus paracasei* |
| *Bacteroides xylanolyticus* | *Lactobacillus paracasei* subsp. *tolerans* |
| *Barnesiella intestinihominis* | *Lactobacillus pentosus* |
| *Bartonella clarridgeiae* | *Lactobacillus plantarum* subsp. *plantarum* |
| *Bartonella quintana* str. *Toulouse* | *Lactobacillus reuteri* |
| *Bifidobacterium adolescentis* | *Lactobacillus rhamnosus* |
| *Bifidobacterium angulatum* | *Lactobacillus rogosae* |
| *Bifidobacterium animalis* | *Lactobacillus ruminis* |
| *Bifidobacterium bifidum* | *Lactobacillus salivarius* |
| *Bifidobacterium breve* | *Lactobacillus ultunensis* |
| *Bifidobacterium catenulatum* | *Lactobacillus vaginalis* |
| *Bifidobacterium coryneforme* | *Lactococcus formosensis* |
| *Bifidobacterium dentium* | *Lactococcus garvieae* |
| *Bifidobacterium faecale* | *Lactococcus lactis* subsp. *Cremoris* |
| *Bifidobacterium gallicum* | *Lactococcus lactis* subsp. *lactis* |
| *Bifidobacterium longum* | *Lactonifactor longoviformis* |
| *Bifidobacterium longum* subsp. *infantis* | *Laribacter hongkongensis* |
| *Bifidobacterium longum* subsp. *longum* | *Lautropia mirabilis* |
| *Bifidobacterium longum* subsp. *suis* | *Leptotrichia buccalis* |
| *Bifidobacterium pseudocatenulatum* | *Leptotrichia hofstadii* |
| *Bifidobacterium pseudolongum* | *Leuconostoc lactis* |
| *Bifidobacterium stercoris* | *Leuconostoc mesenteroides* subsp. *Cremoris* |
| *Bilophila wadsworthia* | *Listeria grayi* |
| *Bittarella massiliensis* | *Listeria monocytogenes* |
| *Blautia coccoides* | *Longicatena caecimuris* |
| *Blautia faecis* | *Marvinbryantia formatexigens* |
| *Blautia glucerasea* | *Megamonas funiformis* |
| *Blautia hansenii* | *Megamonas rupellensis* |
| *Blautia hydrogenotrophica* | *Megasphaera elsdenii* |
| *Blautia luti* | *Megasphaera indica* |
| *Blautia obeum* | *Megasphaera micronuciformis* |
| *Blautia producta* | *Megasphaera paucivorans* |
| *Blautia schinkii* | *Methanobrevibacter smithii* |
| *Blautia stercoris* | *Methanomassiliicoccus luminyensis* |
| *Blautia wexlerae* | *Methanosphaera stadtmanae* |
| *Bradyrhizobium japonicum* | *Methylobacterium radiotolerans* |
| *Burkholderia ambifaria* | *Mitsuokella jalaludinii* |
| *Burkholderia cenocepacia* | *Mitsuokella multacida* |
| *Burkholderia glumae* | *Mobiluncus mulieris* |
| *Burkholderia multivorans* | *Mogibacterium timidum* |
| *Burkholderia plantarii* | *Mogibacterium vescum* |
| *Butyricicoccus faecihominis* | *Moraxella catarrhalis* |
| *Butyricicoccus pullicaecorum* | *Morganella morganii* subsp. *morganii* |
| *Butyricimonas faecihominis* | *Murdochiella asaccharolytica* |

TABLE 8-continued

Exemplary Microbial Strains Found in Human Gut Microbiome

*Butyricimonas paravirosa*
*Butyricimonas virosa*
*Butyrivibrio crossotus*
*Campylobacter coli*
*Campylobacter concisus*
*Campylobacter curvus*
*Campylobacter gracilis*
*Campylobacter hominis*
*Campylobacter jejuni* subsp. *Jejuni*
*Campylobacter showae*
*Campylobacter upsaliensis*
*Candidatus Dorea massiliensis*
Candidatus *Stoquefichus massiliensis*
*Capnocytophaga gingivalis*
*Capnocytophaga sputigena*
*Cardiobacterium hominis*
*Catenibacterium mitsuokai*
*Catonella morbi*
*Cedecea lapagei*
*Citrobacter amalonaticus*
*Citrobacter freundii*
*Citrobacter koseri*
*Citrobacter youngae*
*Clostridium acetobutyricum*
*Clostridium aerotolerans*
*Clostridium aldenense*
*Clostridium aminophilum*
*Clostridium aminovalericum*
*Clostridium amygdalinum*
*Clostridium asparagiforme*
*Clostridium baratii*
*Clostridium bartlettii*
*Clostridium beijerinckii*
*Clostridium bifermentans*
*Clostridium bolteae*
*Clostridium butyricum*
*Clostridium celerecrescens*
*Clostridium cf. saccharolyticum*
*Clostridium citroniae*
*Clostridium clariflavum*
*Clostridium clostridioforme*
*Clostridium cocleatum*
*Clostridium colinum*
*Clostridium difficile*
*Clostridium glycyrrhizinilyticum*
*Clostridium hathewayi*
*Clostridium herbivorans*
*Clostridium hiranonis*
*Clostridium hylemonae*
*Clostridium innocuum*
*Clostridium lactatifermentans*
*Clostridium lavalense*
*Clostridium leptum*
*Clostridium methoxybenzovorans*
*Clostridium methylpentosum*
*Clostridium nexile*
*Clostridium orbiscindens*
*Clostridium oroticum*
*Clostridium perfringens*
*Clostridium polysaccharolyticum*
*Clostridium propionicum*
*Clostridium ramosum*
*Clostridium rectum*
*Clostridium saccharogumia*
*Clostridium saccharolyticum*
*Clostridium sardiniense*
*Clostridium saudii*
*Clostridium scindens*
*Clostridium sordellii*
*Clostridium sphenoides*
*Clostridium spiroforme*
*Clostridium sporogenes*
*Clostridium sticklandii*
*Clostridium straminisolvens*
*Clostridium symbiosum*
*Clostridium tertium*
*Clostridium thermocellum*
*Clostridium xylanolyticum*
*Mycobacterium abscessus*
*Mycobacterium tuberculosis*
*Mycoplasma hominis*
*Neisseria cinerea*
*Neisseria flavescens*
*Neisseria macacae*
*Neisseria mucosa*
*Neisseria sicca*
*Neisseria subflava*
*Nitrobacter hamburgensis*
*Nitrobacter winogradskyi*
*Odoribacter laneus*
*Odoribacter splanchnicus*
*Olsenella profusa*
*Olsenella scatoligenes*
*Olsenella uli*
*Oribacterium sinus*
*Oscillibacter ruminantium*
*Oscillibacter valericigenes*
*Oscillospira guilliermondii*
*Oxalobacter formigenes*
*Paenibacillus jamilae*
*Paenibacillus kribbensis*
*Paenibacillus riograndensis*
*Paeniclostridium sordellii*
*Parabacteroides distasonis*
*Parabacteroides goldsteinii*
*Parabacteroides gordonii*
*Parabacteroides johnsonii*
*Parabacteroides merdae*
*Paraprevotella clara*
*Paraprevotella xylaniphila*
*Parasutterella excrementihominis*
*Parasutterella secunda*
*Parvimonas micra*
*Pediococcus acidilactici*
*Pediococcus pentosaceus*
*Peptoniphilus duerdenii*
*Peptoniphilus grossensis*
*Peptoniphilus harei*
*Peptoniphilus indolicus*
*Peptostreptococcus anaerobius*
*Phascolarctobacterium faecium*
*Phascolarctobacterium succinatutens*
*Porphyromonas asaccharolytica*
*Porphyromonas endodontalis*
*Porphyromonas gingivalis*
*Prevotella bivia*
*Prevotella buccae*
*Prevotella copri*
*Prevotella disiens*
*Prevotella marshii*
*Prevotella melaninogenica*
*Prevotella nigrescens*
*Prevotella pallens*
*Prevotella salivae*
*Prevotella stercorea*
*Prevotella tannerae*
*Prevotella timonensis*
*Propionibacterium acnes*
*Propionibacterium avidum*
*Propionibacterium namnetense*
*Proteus mirabilis*
*Proteus penneri*
*Providencia alcalifaciens*
*Providencia rettgeri*
*Providencia rustigianii*
*Providencia stuartii*
*Pseudoflavonifractor capillosus*
*Ralstonia sp.*
*Robinsoniella peoriensis*
*Roseburia cecicola*
*Roseburia faecis*
*Roseburia hominis*
*Roseburia intestinalis*
*Roseburia inulinivorans*
*Rothia dentocariosa*
*Ruminococcus albus*

TABLE 8-continued

Exemplary Microbial Strains Found in Human Gut Microbiome

Clostridium xylanovorans
Collinsella aerofaciens
Collinsella intestinalis
Collinsella stercoris
Collinsella tanakaei
Coprobacillus cateniformis
Coprobacter fastidiosus
Coprococcus catus
Coprococcus comes
Coprococcus eutactus
Corynebacterium ammoniagenes
Corynebacterium matruchotii
Corynebacterium pseudogenitalium
Corynebacterium tuberculostearicum
Deinococcus radiodurans
Dermabacter hominis
Desuifotomaculum guttoideum
Desulfovibrio legallis
Desulfovibrio piger
Dialister invisus
Dialister microaerophilus
Dialister succinatiphilus
Dielma fastidiosa
Dorea formicigenerans
Dorea longicatena
Dysgonomonas mossii
Edwardsiella tarda
Eggerthella lenta
Eggerthella sinensis
Eikenella corrodens
Eisenbergiella tayi
Enhydrobacter aerosaccus
Enterobacter aerogenes
Enterobacter asburiae
Enterobacter cancerogenus
Enterobacter cloacae
Enterobacter hormaechei
Enterobacter kobei
Enterobacter ludwigii
Enterobacter xiangfangensis
Enterococcus asini
Enterococcus avium
Enterococcus casseliflavus
Enterococcus durans
Enterococcus faecalis
Enterococcus faecium
Enterococcus gallinarum
Enterococcus hirae
Enterococcus mundtii
Enterococcus raffinosus
Enterococcus raffinosus
Erysipelotrichaceae bacterium
Escherichia albertii
Escherichia coli
Escherichia fergusonii
Eubacterium biforme
Eubacterium callanderi
Eubacterium contortum
Eubacterium cylindroides
Eubacterium desmolans
Eubacterium dolichum
Eubacterium eligens
Eubacterium hadrum
Eubacterium hallii
Eubacterium infirmum
Eubacterium limosum
Eubacterium oxidoreducens
Eubacterium ramulus
Eubacterium rectale
Eubacterium ruminantium
Eubacterium saburreum
Eubacterium siraeum
Eubacterium sulci
Eubacterium tortuosum
Eubacterium ventriosum
Ruminococcus bromii
Ruminococcus callidus
Ruminococcus faecis
Ruminococcus gnavus
Ruminococcus lactaris
Ruminococcus obeum
Ruminococcus torques
Ruthenibacterium lactatiformans
Sarcina ventriculi
Sellimonas intestinalis
Senegalimassiiia anaerobia
Shigella boydii
Shigella dysenteriae
Shigella flexneri
Shigella sonnei
Slackia faecicanis
Slackia isoflavoniconvertens
Slackia piriformis
Solobacterium moorei
Staphylococcus caprae
Staphylococcus epidermidis
Staphylococcus hominis subsp. Hominis
Staphylococcus lugdunensis
Staphylococcus warneri
Streptococcus agalactiae
Streptococcus anginosus
Streptococcus anginosus subsp. whileyi
Streptococcus australis
Streptococcus bovis
Streptococcus constellatus subsp. constellatus
Streptococcus equinus
Streptococcus gallolyticus subsp. pasteuri
Streptococcus gallolyticus subsp. pasteurianus
Streptococcus gordonii
Streptococcus gordonii str. Challis
Streptococcus infantarius
Streptococcus infantarius subsp. coli
Streptococcus infantarius subsp. Infantarius
Streptococcus infantis
Streptococcus lactarius
Streptococcus lutetiensis
Streptococcus mutans
Streptococcus parasanguinis
Streptococcus pasteurianus
Streptococcus pleomorphus
Streptococcus rubneri
Streptococcus salivarius
Streptococcus salivarius subsp. salivarius
Streptococcus sanguinis
Streptococcus thermophilus
Streptococcus vestibularis
Subdoligranulum variabile
Succinatimonas hippei
Sutterella parvirubra
Sutterella stercoricanis
Sutterella wadsworthensis
Terrisporobacter glycolicus
Turicibacter sanguinis
Ureaplasma parvum
Vagococcus penaei
Varibaculum cambriense
Veillonella sp.
Veillonella dispar
Veillonella parvula
Veillonella rogosae
Veillonella tobetsuensis
Vibrio cholerae
Vibrio furnissii
Vibrio mimicus
Victivallis vadensis
Weissella cibaria
Weissella confusa
Weissella paramesenteroides
Xenorhabdus nematophila
Yersinia enterocolitica subsp. Palearctica TABLE 8-continued Exemplary Microbial Strains Found in Human Gut Microbiome

*Eubacterium xylanophilum*　　*Yersinia pseudotuberculosis*
*Eubacterium yurii subsp. Margaretiae*

Example 3: Exemplary System for Characterizing Microbial Strains that Affect HIF Pathway

Example 3.1: HIF Pathway

Hypoxia inducible factor (HIF) pathway mediates a diversity of metabolic and physiological adaptations to reduced oxygen levels in cells. Activation of the HIF pathway promotes erythropoiesis and angiogenesis to reduce the cellular requirement for oxygen. Though the HIF pathway is important for cellular stress response, constitutive activation of HIF-1 leads to neovascularization in conditions such as diabetic retinopathy, retinopathy of prematurity, age-related macular degeneration, and glaucoma. Thus, developing modulators of HIF pathway is essential for the treatment of ocular neovascular diseases.

Figure 7:
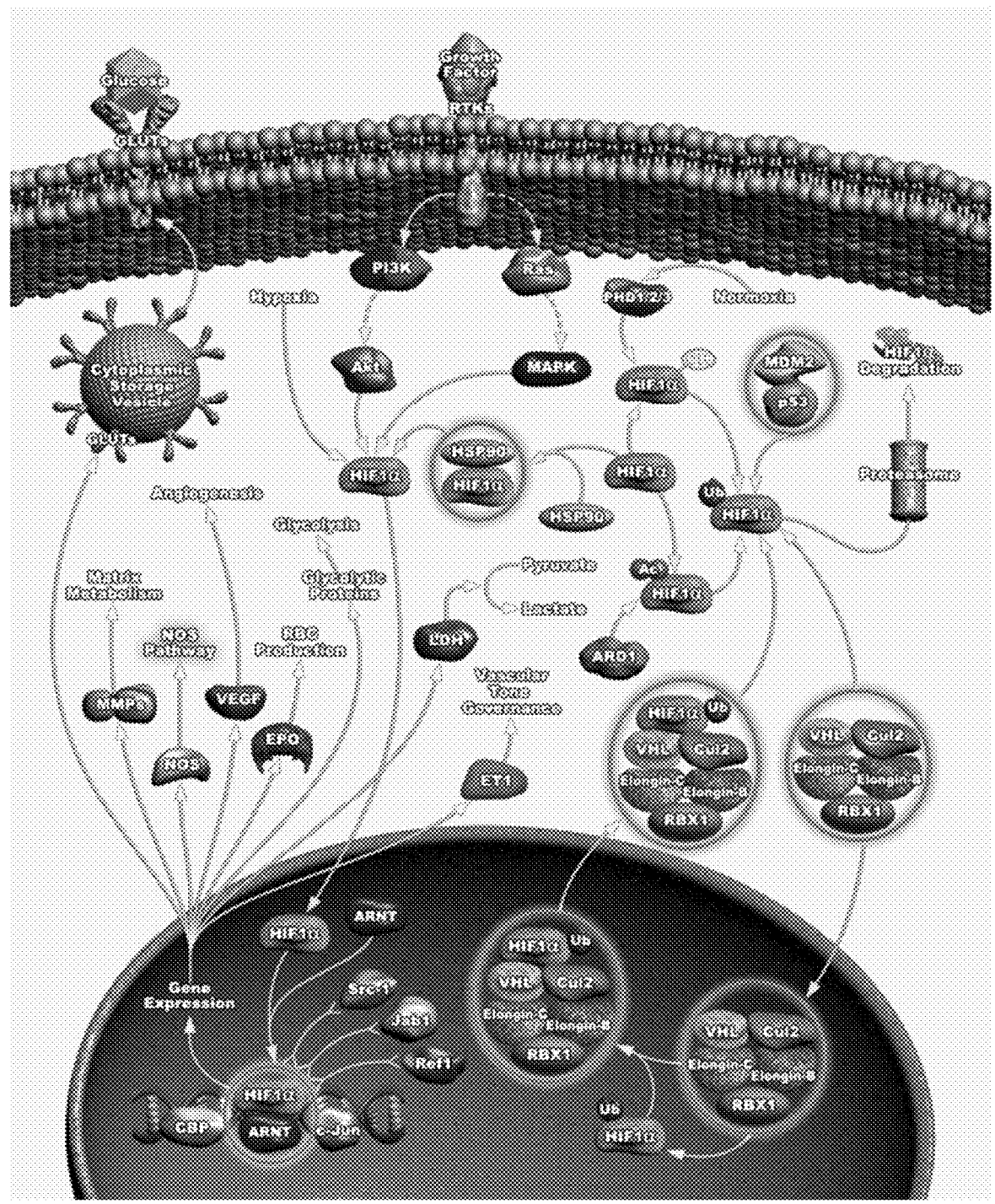
FIG. 7 includes a schematic of the exemplary HIF pathways.

The HIF-1 pathway consists of the HIF transcription factor and the negative regulator, the prolyl hydroxylase EGLN. EGLN functions as oxygen sensor and in the presence of oxygen it hydroxylates the HIF α-subunit (HIFα). Hydroxylation of HIFα leads to binding to von Hippel-Lindau (VHL) E3 ubiquitin ligase, among other factors, which promote HIFα degradation (see FIG. 7). Under low oxygen conditions, HIFα protein is stabilized and it promotes transcriptional activation of genes required for adaptation to low oxygen levels.

Example 3.2: Constitutively Active HIF-1 Results in Defect in Egg Laying

In *C. elegans*, egl-9 encodes the EGLN homolog. In egl-9 loss-of-function (egl-9 lf) *C. elegans* mutants, HIF-1, which is the homolog of HIF1α, protein levels are stabilized. Thus, the HIF1 protein is constitutively active leading to continuous activity of HIF-1 transcriptional target genes. To identify microbes that regulate HIF-1 pathway, egl-9 loss-of-function (egl-9 lf) *C. elegans* mutants were analyzed. egl-9 lf mutant *C. elegans* have constitutively active HIF-1, which results in them being defective in laying eggs. Therefore, they become bloated with eggs as adults.

Example 3.3: Microbial Strains Affect HIF-1 Induced Egg Laying Defects

HIF-1 modulators were identified by screening individual bacterial strains for the ability to suppress the egg laying defect of egl-9 lf mutant. While wildtype animals lay 8±2 (n=30) eggs per hour, egl-9 lf mutants lay 2±1 (n=30) eggs/hour. The egl-9 lf *C. elegans* mutants were administered with each individual microbe and the respective egg-laying rate was measured. In this assay, it was found that *Gluconacetobacter* spp and *Bifidobacterium* spp significantly enhanced the egg-laying rate of egl-9 lf *C. elegans* mutants to 11±2 (n=25) and 8±2 (n=29) respectively (see Table 9). This example demonstrates that microbial strains, such as those in Table 9, can modulate HIF-1 and a HIF-1 pathway, and can be used to ameliorate conditions and diseases associated with an alteration of a HIF-1 pathway.

TABLE 9

| egl-9 lf C. elegans administered with | Egg-laying rate | Number of animals tested |
|---|---|---|
| E. coli OP50-1 | 2 ± 1 | 30 |
| Gluconacetobacter hansenii | 11 ± 2 | 25 |
| Terrisporobacter glycolicus | 3 ± 1 | 32 |
| Coprococcus sp. | 1 ± 1 | 28 |
| L. plantarum | 2 ± 2 | 29 |
| Clostridium butyricum | 3 ± 1 | 31 |
| Paenibacillus barengoltzii | 1 ± 2 | 27 |
| Veillonella atypica | 1 ± 1 | 30 |
| Bifidobacterium | 8 ± 2 | 29 |
| Bacillus subtilis | 4 ± 2 | 28 |
| Acidaminococcus sp | 3 ± 2 | 31 |

Other Embodiments

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

It is to be understood that while embodiments of the invention have been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system, comprising:

a plurality of *C. elegans* cultures, wherein each culture comprises a transgenic *C. elegans* strain that models a mammalian disease or condition, wherein one or more of the cultures comprises a transgenic *C. elegans* strain that models Alzheimer's disease, wherein the transgenic *C. elegans* strain comprises a transgene comprising a human APOE4 gene, a human Aβ$_{1-42}$ gene, a human Aβ$_{3-42}$ gene, a human tau gene, a human pseudophosphorylated tau gene, a pseudohyperphosphorylated human tau gene, or a portion thereof, and wherein each of the cultures includes one or more microbes of a human microbiome.

2. The system of claim 1, wherein the plurality of *C. elegans* cultures comprises:

(a) 5 or more *C. elegans* cultures, (b) 10 or more *C. elegans* cultures, (c) 25 or more *C. elegans* cultures, or (d) 50 or more *C. elegans* cultures.

3. The system of claim 1, wherein one or more of the cultures comprises a transgenic *C. elegans* strain that comprises a transgene comprising a reporter gene.

4. The system of claim 1, wherein one or more of the cultures comprises a transgenic *C. elegans* strain that comprises a transgene comprising a mammalian DNA regulatory element associated with a mammalian disease or condition.

5. The system of claim 1, wherein one or more of the cultures comprises a transgenic *C. elegans* strain that comprises a transgene encoding a mammalian RNA regulatory element associated with a mammalian disease or condition.

6. The system of claim 1, wherein two or more of the cultures comprise transgenic *C. elegans* strains that model the same mammalian disease or condition.

7. The system of claim 1, wherein all of the cultures comprise a transgenic *C. elegans* strain that models the same mammalian disease or condition.

8. The system of claim 1, wherein all of the cultures comprise the same transgenic *C. elegans* strain.

9. The system of claim 1, wherein two or more of the cultures comprise transgenic *C. elegans* strains that model different mammalian diseases or conditions.

10. The system of claim 1, wherein the microbiome is a cutaneous microbiome, an oral microbiome, a nasal microbiome, a gastrointestinal microbiome, a brain microbiome, a pulmonary microbiome, a microbiome, or a urogenital microbiome.

11. The system of claim 1, wherein the microbes in each culture comprise one or more microbial strains.

12. The system of claim 1, wherein the microbes in each culture comprise a single microbial strain.

13. The system of claim 1, wherein one or more of the cultures comprise a therapeutic or nutraceutical agent.

14. A method, comprising:
adding microbes obtained from a mammalian microbiome to each culture of a system,
wherein the system, comprises a plurality of *C. elegans* cultures,
wherein each culture comprises a transgenic *C. elegans* strain that models a mammalian disease or condition,
wherein one or more of the cultures comprises a transgenic *C. elegans* strain that models Alzheimer's disease, wherein the transgenic *C. elegans* strain comprises a transgene comprising a human APOE4 gene, a human $A\beta_{1-42}$ gene, a human $A\beta_{3-42}$ gene, a human tau gene, a human pseudophosphorylated tau gene, a pseudohyperphosphorylated human tau gene, or a portion thereof, and
wherein each of the cultures includes one or more microbes of a human microbiome.

15. The method of claim 14, wherein the microbes added to each culture comprise one or more microbial strains.

16. The method of claim 14, wherein the microbes added to each culture comprise a single microbial strain.

17. The method of claim 14, wherein one or more of the cultures comprise a therapeutic or nutraceutical agent.

18. The method of claim 14, further comprising determining one or more parameters of a transgenic *C. elegans* strain in each of the cultures, wherein the one or more parameters are associated with the mammalian disease or condition that the transgenic *C. elegans* strain models, and wherein the one or more parameters comprises a protein, a polypeptide, or a transcript.

19. The method of claim 14, further comprising determining one or more parameters of a transgenic *C. elegans* strain in each of the cultures, wherein the one or more parameters are associated with the mammalian disease or condition that the transgenic *C. elegans* strain models, and wherein the one or more parameters comprises a level of an activity of the transgenic *C. elegans* strain.

20. A method, comprising:
adding a plurality of microbial strains of a mammalian microbiome to a plurality of *C. elegans* cultures,
wherein a different microbial strain is added to each *C. elegans* culture,
wherein each culture comprises the same transgenic *C. elegans* strain, wherein the transgenic *C. elegans* strain models Alzheimer's disease, wherein the transgenic *C. elegans* strain comprises a transgene comprising a human APOE4 gene, a human $A\beta_{1-42}$ gene, a human $A\beta_{3-42}$ gene, a human tau gene, a human pseudophosphorylated tau gene, a pseudohyperphosphorylated human tau gene, or a portion thereof, and
wherein each of the cultures includes one or more microbes of a human microbiome.

\* \* \* \* \*

SEQUENCE LISTING

<160> NUMBER OF SEQ ID NOS: 8

<210> SEQ ID NO 1
<211> LENGTH: 51

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtaagtttaa acatatatat actaactaac cctgattatt taaattttca g            51

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtaagtttaa acagttcggt actaactaac catacatatt taaattttca g            51

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtaagtttaa acatgatttt actaactaac taatctgatt taaattttca g            51

<210> SEQ ID NO 4
<211> LENGTH: 63
<212> TYPE: DNA
<213> ORGANISM: Caenorhabditis elegans

<400> SEQUENCE: 4
atgactctgc tctaccaagt agggttatta ctccttgtgg cagctactta taaggtgtcg   60
gca                                                                63

<210> SEQ ID NO 5
<211> LENGTH: 1600
<212> TYPE: DNA
<213> ORGANISM: Caenorhabditis elegans

<400> SEQUENCE: 5
actaactgac attaggtgtc acacaaaaga aatcacacac tatacatcaa aatatacatc   60
acaagtgagt caatacaatc cgggtgaagc tcaagaatgg atttcgcaga cttcttctgc  120
tcattggctg cttcgaaaac ctgaatagtt tatattaaac tagtgaaatc gaattcatac  180
aaacctgttt cgattcacta cttttcaatc gatggtcaaa cgtagaatca aaaacacgtg  240
tcagaaacac ttccaatcat caaaatgatc catcaattcc actcggagca acaatttcga  300
agcctgggaa tgtgtgtggt gagcacttttg ggctctggta gagcatgtac ctttataggt  360
gcgctctacg caattcacca gctgaacaat ggagttgagc ctaatgtaac taaaaattta  420
tttgaatgct ttacaaaaat attatttcag atcttcgaga tcatgaaaac tatcaaacag  480
cagcgccctg gagcaatcga gtcgttccca caatattcag gtgtatatgc aatcgtttta  540
gactacattt cggtaagttg ctacttcaga gataaactgt aattatttta aatttcagcg  600
caaacgcgga ggaaagtctg atcctgttaa caaatacata aatcgtttcc tcgctgatct  660
cacggagata ttgccagcat gctcaacgtt gccagtgatg aatccaagca cagaactgca  720
```

```
ttaagtatac tatttattac tcgatacttt tgttcacata ggttttttaa atcatatttt      780
atgcatcatt tatcatattc aatgcatcat tcatatcata gtcaataaaa aggttgattt      840
ctcatgttct ggtttcaaat gctgactttg gtaaaagaa cgcgtgcctg cctattgcct       900
atcttggcat tttctcgata aattttaaaa tgtaggttcg atcttatgag atttgtagtc      960
aaaagagctc atatgtattc aggtaggtct ggtagcgaga ccaacttaat agcatgacaa     1020
gcattttcaa tttgccctgg agcgcaattg gttttttatt cgaaaatcgc acatttctgt     1080
ttccccataa tataaaattt ccaggacgat atatattaca ttcttcacaa aatattgcat     1140
tacagacacc gacaaagaat ctccacctga tatgaaaaca atgagccaac aatgttatct     1200
gtattgccac cacccacatt tcctagtcat tcagtatata ttgtttcaat tgaatcattg     1260
caggtatata tcgaattgaa cttgtaaggc ttcatcttca tttctcaata catcatccat     1320
cattccagag cagctccggc cacacaaaaa ttggtggcgg tctgatattg ataatcgact     1380
tctttgacgt gcctgacgga gcagcaaagc ggagcactga taagacaatg aagaactaaa     1440
aaattgtctt cggttttcag tctttagttc tgcagcactt tattttttgt ttctcctatt     1500
tttccgcatt ttcctaactt tctgatgtcc atttcaaatg attttgtta taaaattgtt      1560 taatttcagg gcgactaaaa cctaccaaaa cccataaaaa                            1600

<210> SEQ ID NO 6
<211> LENGTH: 1107
<212> TYPE: DNA
<213> ORGANISM: Homo sapiens

<400> SEQUENCE: 6
atgaaggtcc tttgggccgc ccttcttgtc accttccttg ctggatgcca agctaaggtt       60
gagcaagctg ttgaaactga gccagagcca gagcttcgtc aacaaactga gtggcaatct      120
ggacaacgtt gggagcttgc tcttggacgt ttctgggact accttcgttg ggttcaaacc      180 cttttccgagc aagttcaaga ggagcttctt tcttcccaag ttacccaaga gcttcgtgct     240
cttatggatg agactatgaa ggtaagttta aacatatata tactaactaa ccctgattat      300
ttaaattttc aggagcttaa ggcttacaag tctgagcttg aggagcaact taccccagtt      360
gctgaggaga cccgtgctcg tctttccaag gtaagtttaa acagttcggt actaactaac      420
catacatatt taaattttca ggagcttcaa gctgctcaag ctcgtcttgg agctgatatg      480
gaggatgttc gtggacgtct tgttcaatac cgtggagagg ttcaagctat gcttggacaa      540
tctaccgagg agcttcgtgt tcgtcttgcc tccaccttc gtaagcttcg taagcgtctt       600
cttcgtgacg ctgacgacct tcaaaagcgt cttgctgtct accaagctgg agctcgtgag      660
ggagctgagc gtgacttc cgctatccgt gagcgtcttg gaccacttgt tgagcaagga       720
cgtgttcgtg ctgctaccgt cggatccctt gctggacaac cacttcaaga gcgcgctcaa      780
gcttggggag agcgtcttcg tgctcgcatg gaggagatgg gatctcgcac ccgtgatcgt     840
cttgatgagg ttaaggtaag tttaaacatg attttactaa ctaactaatc tgatttaaat     900
tttcaggagc aagttgctga ggtccgtgct aagcttgaag agcaagctca acaaatccgt     960
cttcaagctg aggctttcca agctcgtctt aagtcttggt tcgagccact tgttgaggat    1020
atgcaacgtc aatgggctgg acttgttgag aaggtccaag ccgctgtcgg aacctccgct    1080
gctccagttc catccgataa ccactaa                                        1107

<210> SEQ ID NO 7
```

```
<211> LENGTH: 297
<212> TYPE: DNA
<213> ORGANISM: Caenorhabditis elegans

<400> SEQUENCE: 7
atgcaagatc ctttcaagca ttcccttctt ctctatcact cttctttctt tttgtcaaaa      60
aattctctcg ctaatttatt tgctttttta atgttattat tttatgactt tttatagtca     120
ctgaaaagtt tgcatctgag tgaagtgaat gctatcaaaa tgtgattctg tctgatgtac     180
tttcacaatc tctcttcaat tccattttga agtgctttaa acccgaaagg ttgagaaaaa     240
tgcgagcgct caaatatttg tattgtgttc gttgagtgac caacaaaaa gaggaaa        297

<210> SEQ ID NO 8
<211> LENGTH: 1167
<212> TYPE: DNA
<213> ORGANISM: Homo sapiens

<400> SEQUENCE: 8
atgactctgc tctaccaagt agggttatta ctccttgtgg cagctactta taaggtgtcg      60
gcaaaggtcc tttgggccgc ccttcttgtc accttccttg ctggatgcca agctaaggtt    120
gagcaagctg ttgaaactga gccagagcca gagcttcgtc aacaaactga gtggcaatct    180
ggacaacgtt gggagcttgc tcttggacgt ttctgggact accttcgttg ggttcaaacc    240 cttttccgagc aagttcaaga ggagcttctt tcttcccaag ttacccaaga gcttcgtgct    300
cttatggatg agactatgaa ggtaagttta aacatatata tactaactaa ccctgattat    360
ttaaattttc aggagcttaa ggcttacaag tctgagcttg aggagcaact taccccagtt    420
gctgaggaga cccgtgctcg tctttccaag gtaagtttaa acagttcggt actaactaac    480
catacatatt taaattttca ggagcttcaa gctgctcaag ctcgtcttgg agctgatatg    540
gaggatgttc gtggacgtct tgttcaatac cgtggagagg ttcaagctat gcttggacaa    600
tctaccgagg agcttcgtgt tcgtcttgcc tcccaccttc gtaagcttcg taagcgtctt    660
cttcgtgacg ctgacgacct tcaaaagcgt cttgctgtct accaagctgg agctcgtgag    720
ggagctgagc gtggactttc cgctatccgt gagcgtcttg gaccacttgt tgagcaagga    780
cgtgttcgtg ctgctaccgt cggatccctt gctggacaac cacttcaaga gcgcgctcaa    840
gcttggggag agcgtcttcg tgctcgcatg gaggagatgg gatctcgcac ccgtgatcgt    900
cttgatgagg ttaaggtaag tttaaacatg attttactaa ctaactaatc tgatttaaat    960
tttcaggagc aagttgctga ggtccgtgct aagcttgaag agcaagctca acaaatccgt   1020
cttcaagctg aggctttcca agctcgtctt aagtcttggt tcgagccact tgttgaggat   1080
atgcaacgtc aatgggctgg acttgttgag aaggtccaag ccgctgtcgg aacctccgct   1140
gctccagttc catccgataa ccactaa                                        1167
```